US012622743B2

(12) United States Patent
Won et al.

(10) Patent No.: US 12,622,743 B2
(45) Date of Patent: May 12, 2026

(54) TISSUE ABLATION DEVICE, IMAGE GENERATION MODULE, AND TISSUE ABLATION SYSTEM COMPRISING SAME

(71) Applicant: INTEKMEDI, Sejong-si (KR)

(72) Inventors: Young Jae Won, Sejong-si (KR); Ki Sub Kim, Chungcheongbuk-do (KR); Yu Kyeong Chae, Sejong-si (KR)

(73) Assignee: INTEKMEDI, Sejong-si (KR)

( * ) Notice: Subject to any disclaimer, the term of this patent is extended or adjusted under 35 U.S.C. 154(b) by 1044 days.

(21) Appl. No.: 17/774,183

(22) PCT Filed: Nov. 2, 2020

(86) PCT No.: PCT/KR2020/015113
§ 371 (c)(1),
(2) Date: May 4, 2022

(87) PCT Pub. No.: WO2021/091176
PCT Pub. Date: May 14, 2021

(65) Prior Publication Data
US 2022/0370118 A1      Nov. 24, 2022

(30) Foreign Application Priority Data

| | | |
|---|---|---|
| Nov. 4, 2019 | (KR) | 10-2019-0139548 |
| Dec. 11, 2019 | (KR) | 10-2019-0164737 |
| Dec. 11, 2019 | (KR) | 10-2019-0164738 |

(51) Int. Cl.
*A61B 18/14* (2006.01)
*A61B 17/32* (2006.01)
(Continued)

(52) U.S. Cl.
CPC .. *A61B 18/1445* (2013.01); *A61B 17/320092* (2013.01); *A61B 2017/00057* (2013.01);
(Continued)

(58) Field of Classification Search
CPC ...... A61B 18/1445; A61B 2017/00057; A61B 2018/00982
See application file for complete search history.

(56) References Cited

U.S. PATENT DOCUMENTS

2003/0171747 A1* 9/2003 Kanehira ............. A61B 18/085
                                                                 606/45
2013/0253489 A1* 9/2013 Nau, Jr. ................. A61B 18/22
                                                                 606/17
(Continued)

FOREIGN PATENT DOCUMENTS

JP      2015-512713      4/2015
JP      2016-526999      9/2016
(Continued)

OTHER PUBLICATIONS

International Search Report and the Written Opinion Dated Jun. 8, 2021 From the International Searching Authority Re. Application No. PCT/KR2020/015113 and Its Translation Into English. (14 Pages).

*Primary Examiner* — Linda C Dvorak
*Assistant Examiner* — Ryan T Clark

(57) ABSTRACT

An ablation device includes a first jaw, a second jaw including an ablation unit including a protrusion for ablating a tissue and being rotatable with respect to the first jaw under the first jaw, and a signal unit configured to provide a signal to the tissue and receive a reflected signal and disposed on the second jaw, in which the signal unit moves in a longitudinal direction of the ablation unit, the first jaw does not overlap the signal unit in a vertical direction, and the second jaw overlaps the signal unit in the vertical direction.

14 Claims, 26 Drawing Sheets

(51) Int. Cl.
    *A61B 17/00*          (2006.01)
    *A61B 18/00*          (2006.01)

(52) U.S. Cl.
    CPC ............. *A61B 2017/320069* (2017.08); *A61B*
             *2018/00404* (2013.01); *A61B 2018/00577*
             (2013.01); *A61B 2018/00982* (2013.01)

(56)                References Cited

U.S. PATENT DOCUMENTS

| | | | |
|---|---|---|---|
| 2014/0135804 A1* | 5/2014 | Weisenburgh, II ... | F15D 1/0015 606/169 |
| 2016/0066915 A1* | 3/2016 | Baber .................... | A61B 17/32 227/178.1 |
| 2016/0066916 A1 | 3/2016 | Overmyer et al. | |

FOREIGN PATENT DOCUMENTS

| | | |
|---|---|---|
| JP | 2017-530840 | 10/2017 |
| KR | 10-2017-0051876 | 5/2017 |
| KR | 10-2019-0050057 | 5/2019 |

* cited by examiner

[FIG. 1]
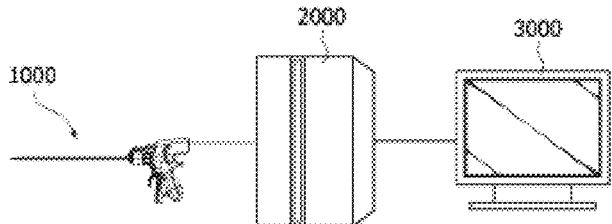
[FIG. 2]
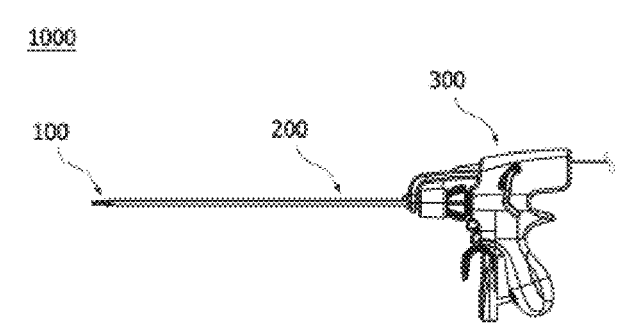
[FIG. 3]
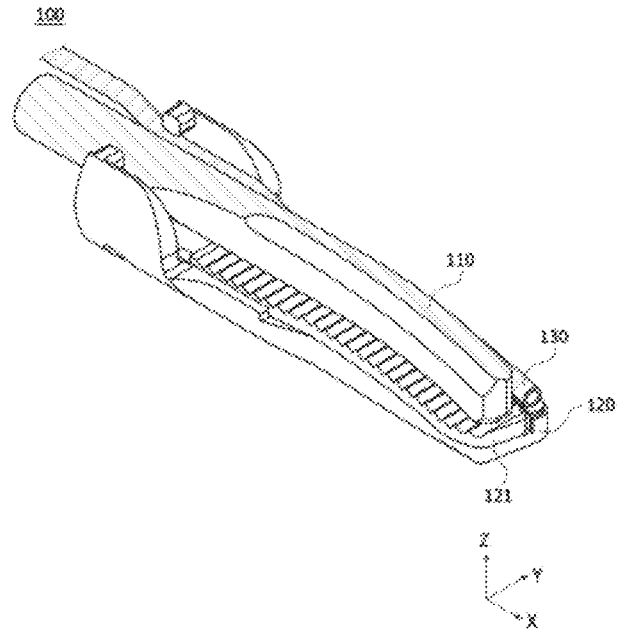

[FIG. 4]
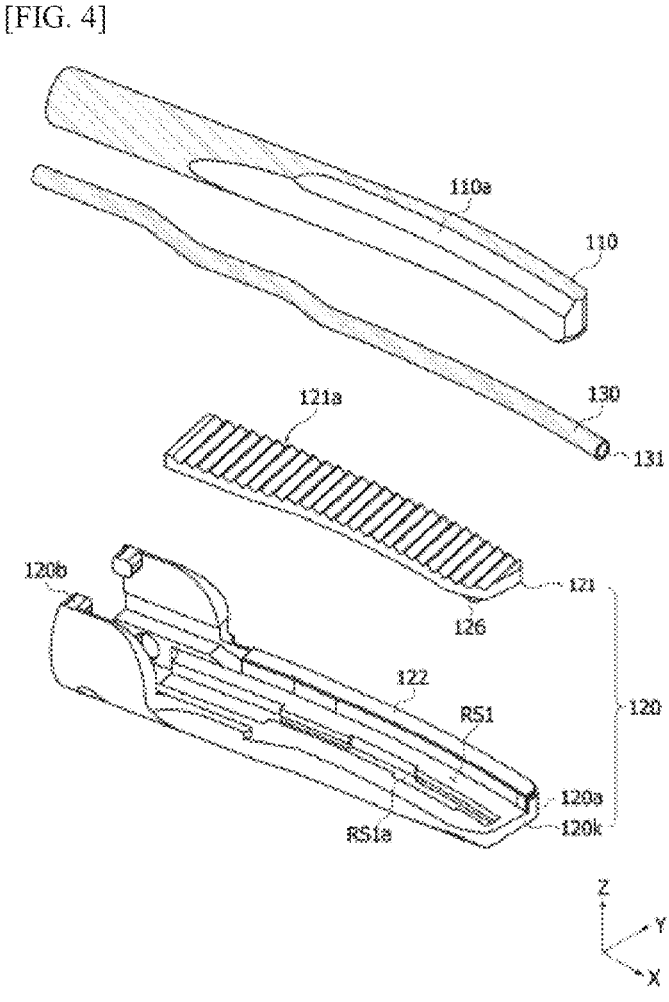

[FIG. 5]
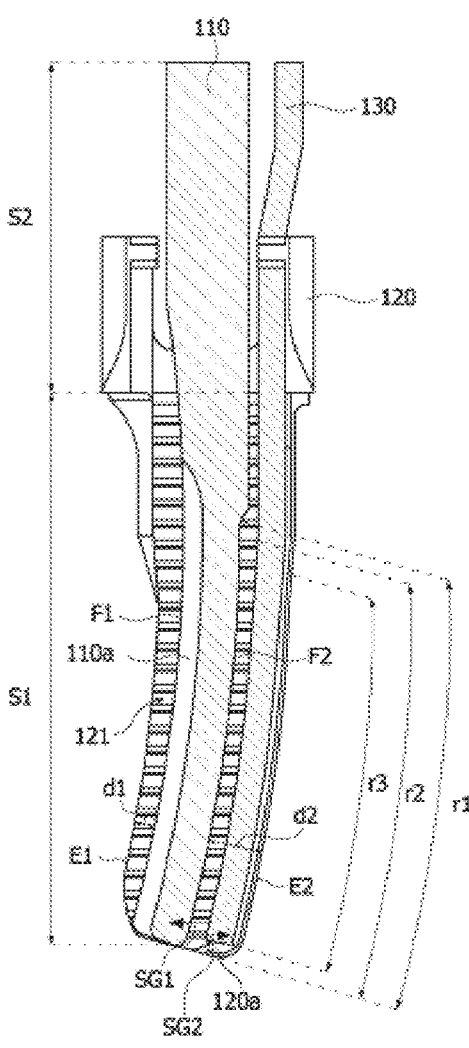

[FIG. 6]
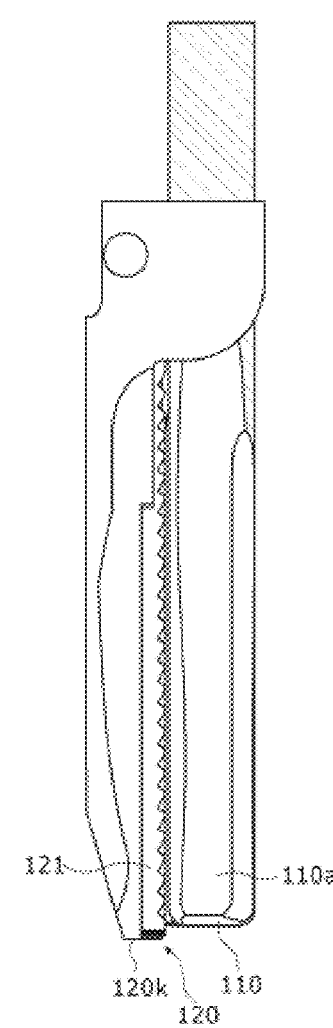

[FIG. 7]

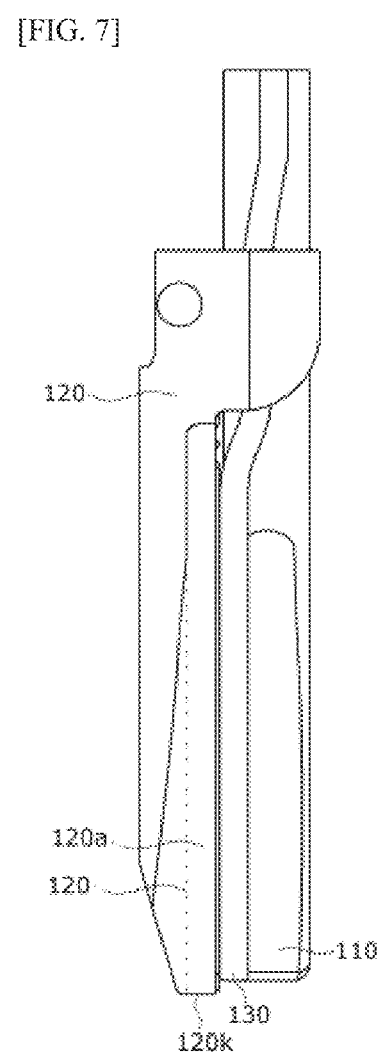

[FIG. 8]
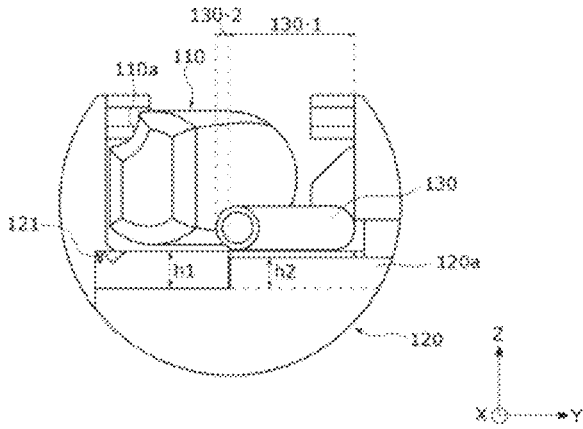
[FIG. 9]
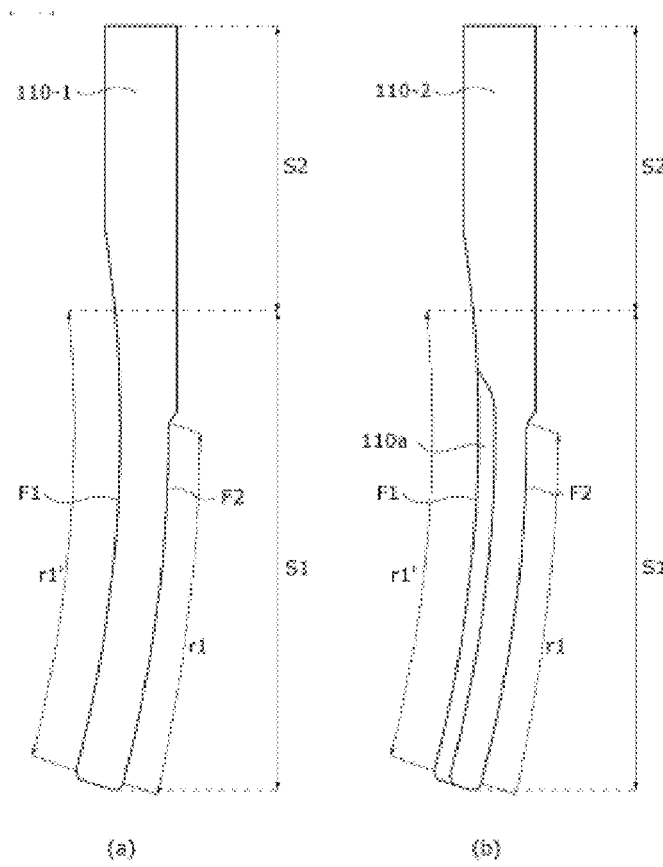
(a)                    (b)

[FIG.10]
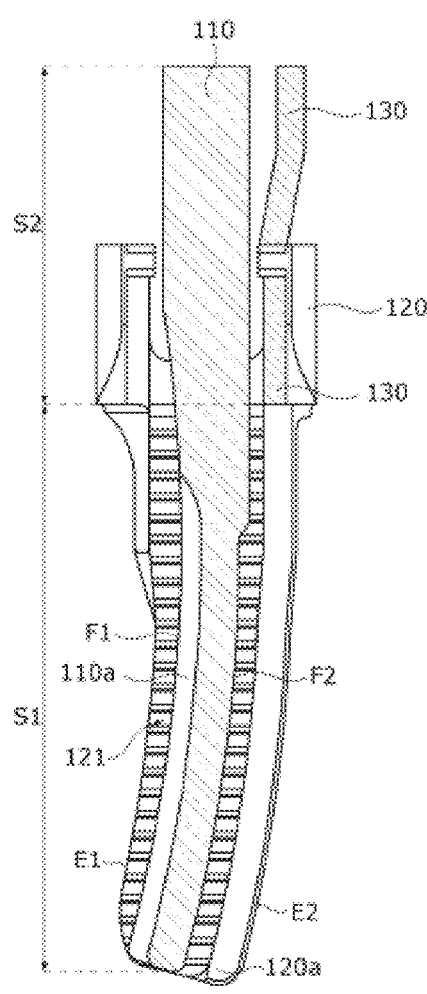

[FIG.11]
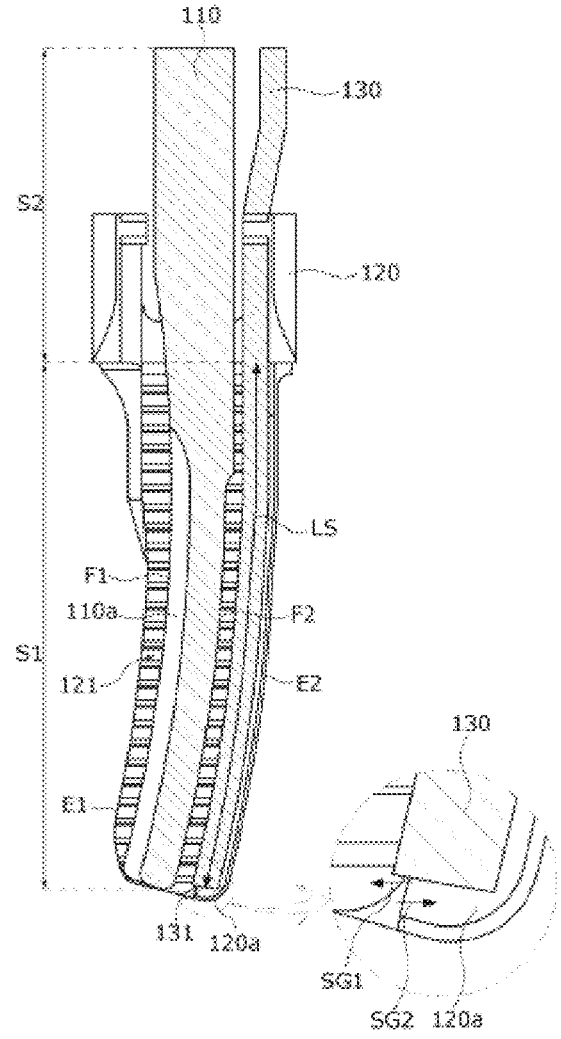

[FIG.12]
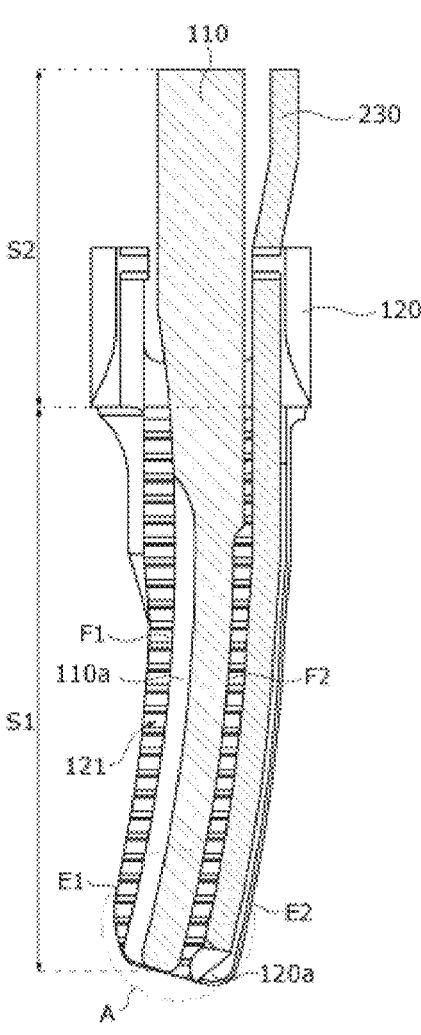

[FIG.13]
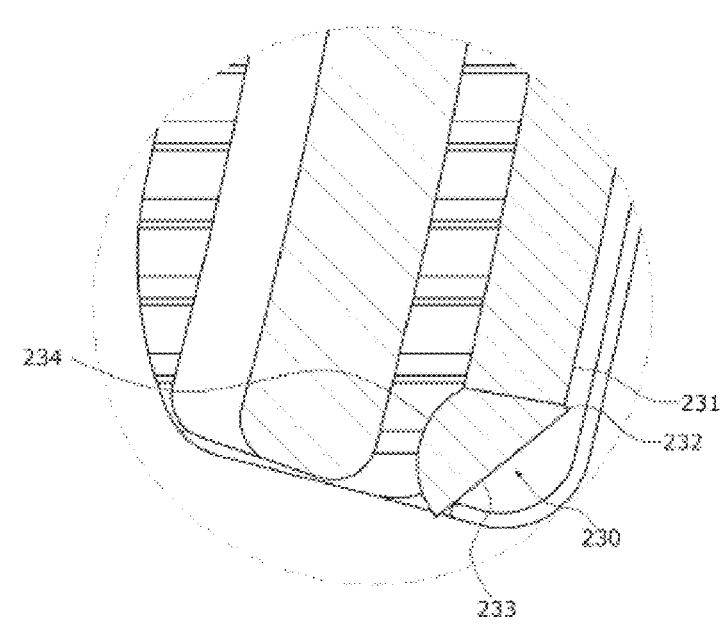

[FIG.14]
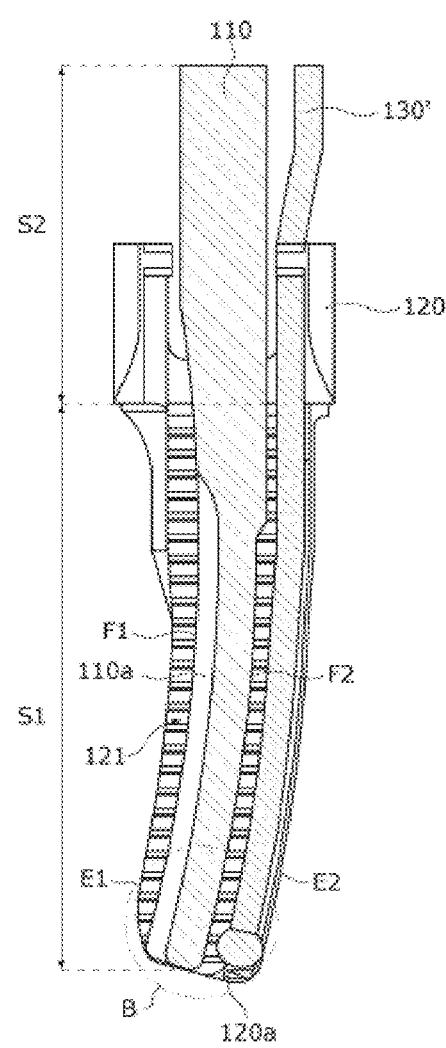

[FIG.15]
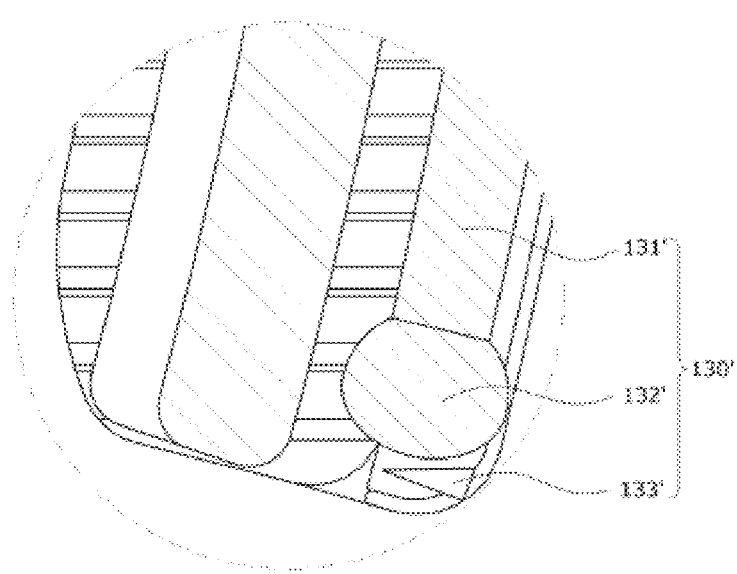

[FIG.16]
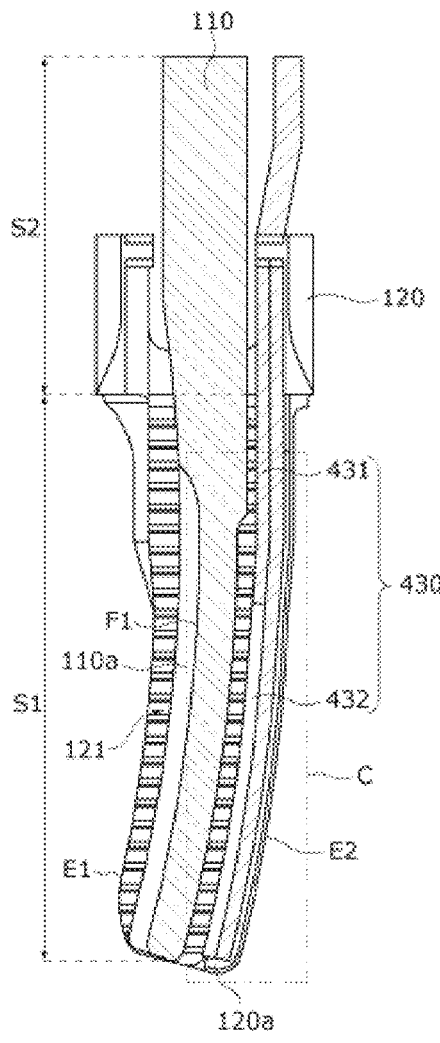

[FIG.17]
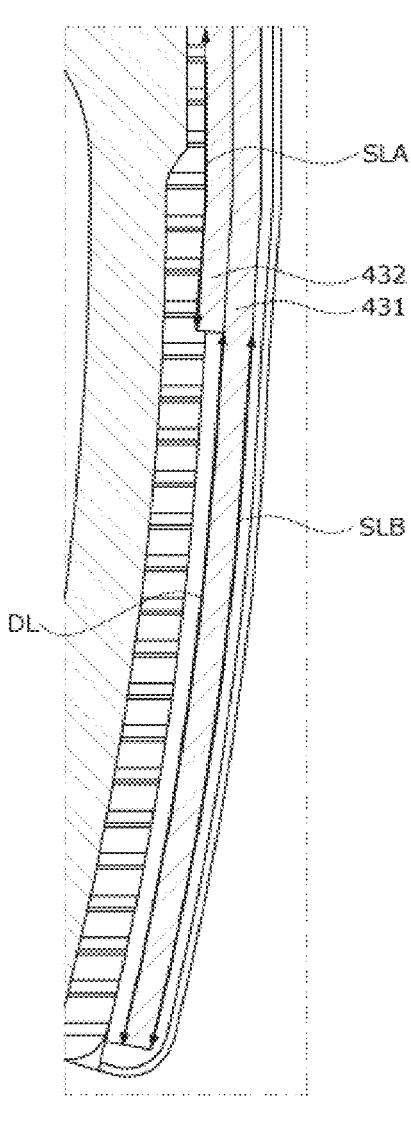

[FIG.18]
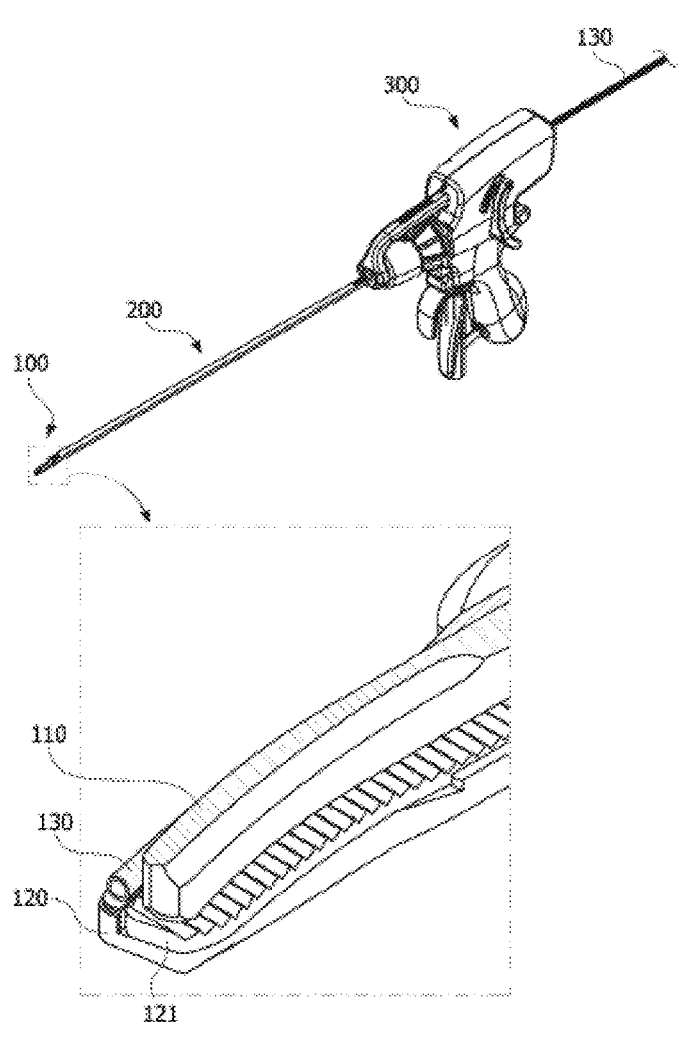

[FIG.19]
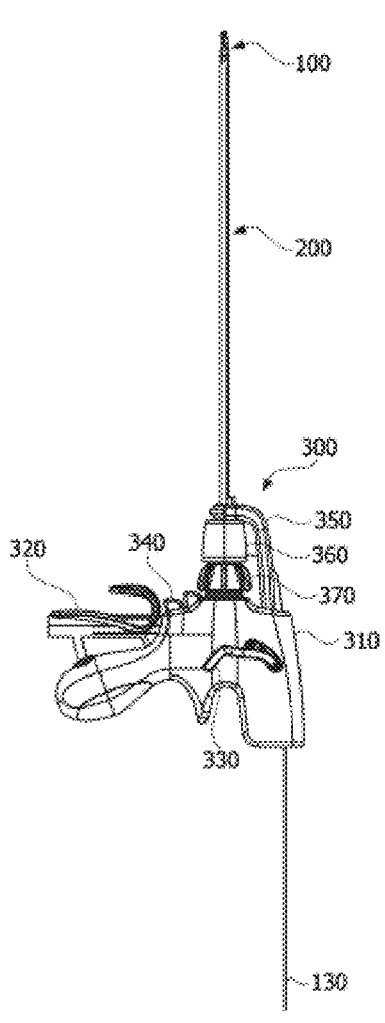

[FIG.20]
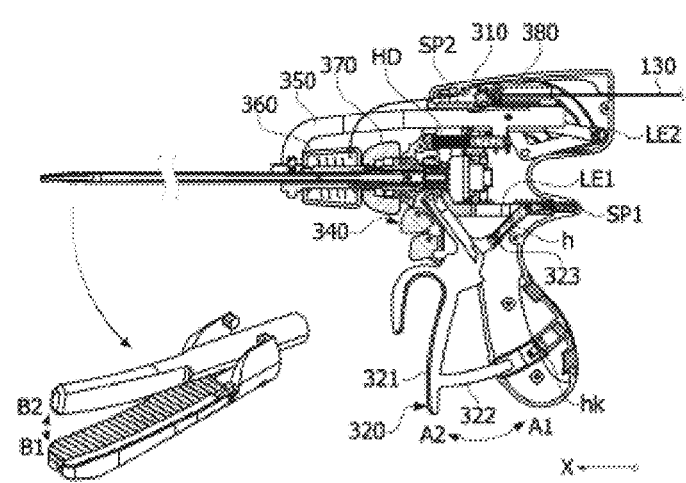
[FIG.21]
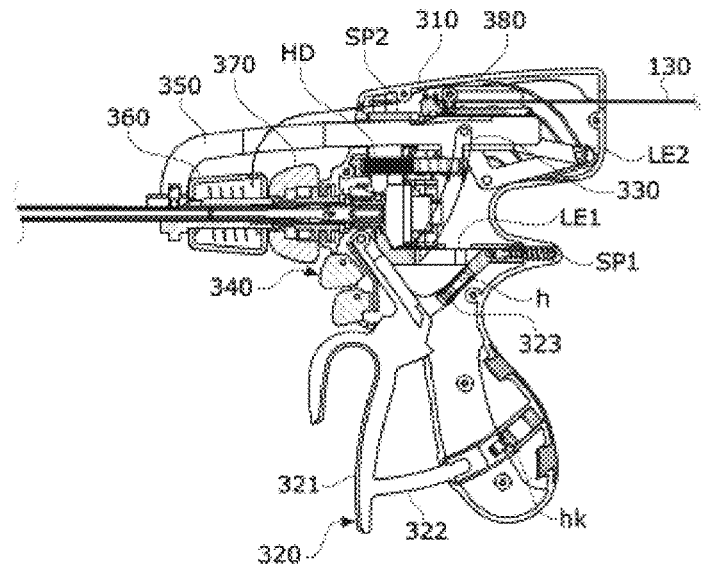

[FIG.22]
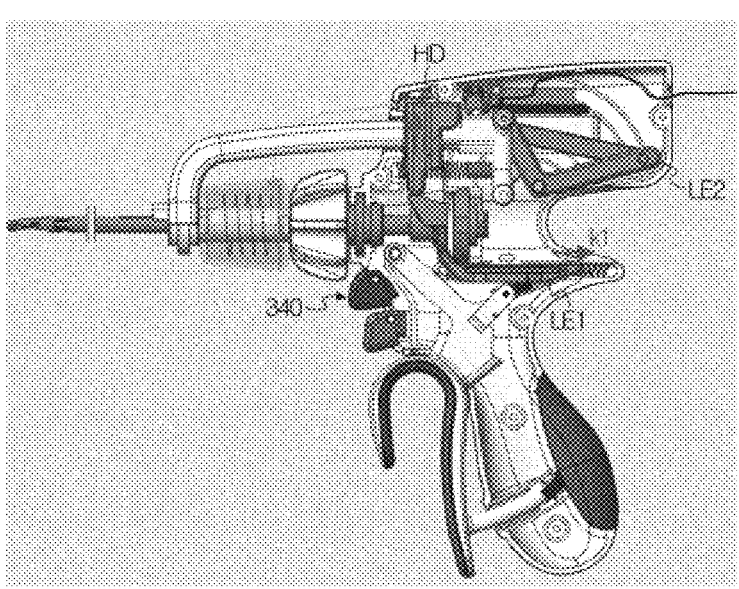
[FIG.23]
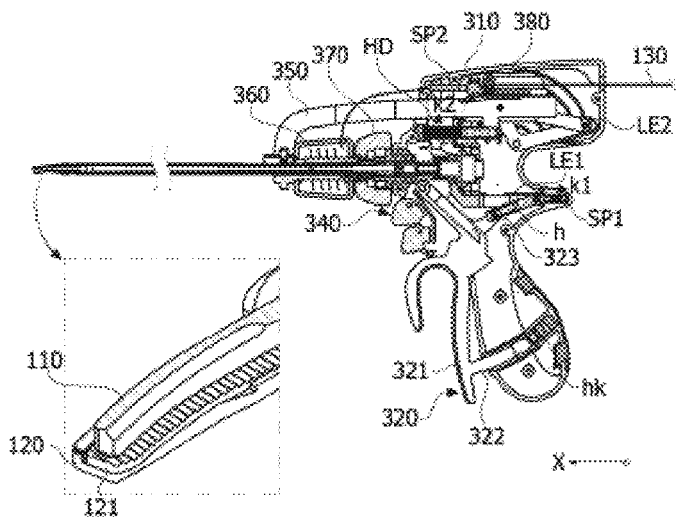

[FIG.24]
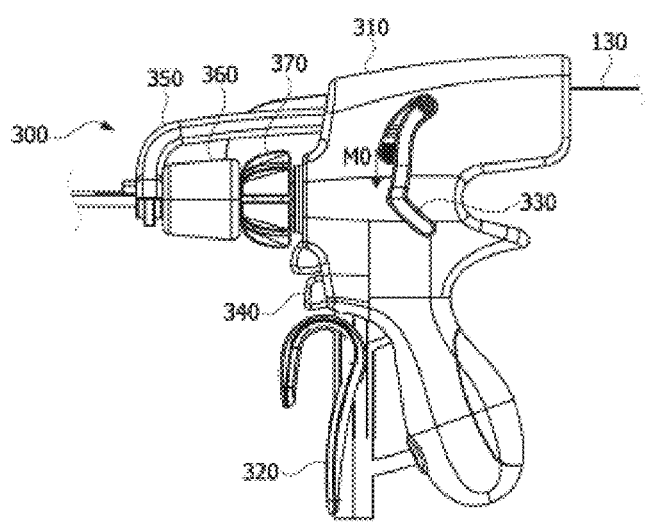
[FIG.25]
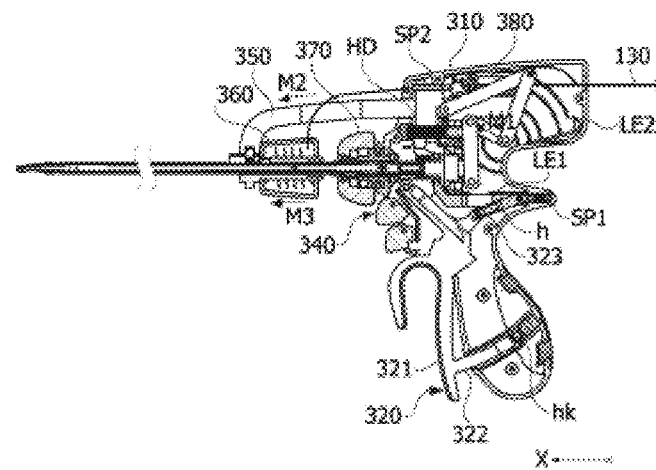

[FIG.26]
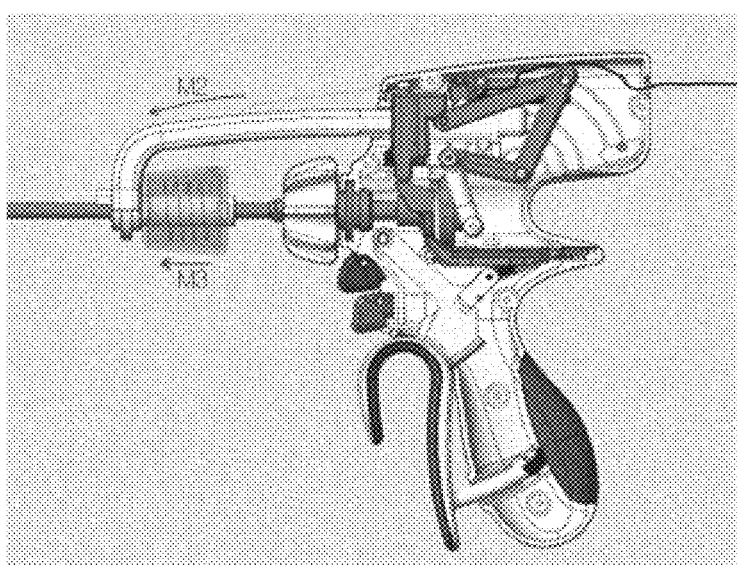
[FIG.27]
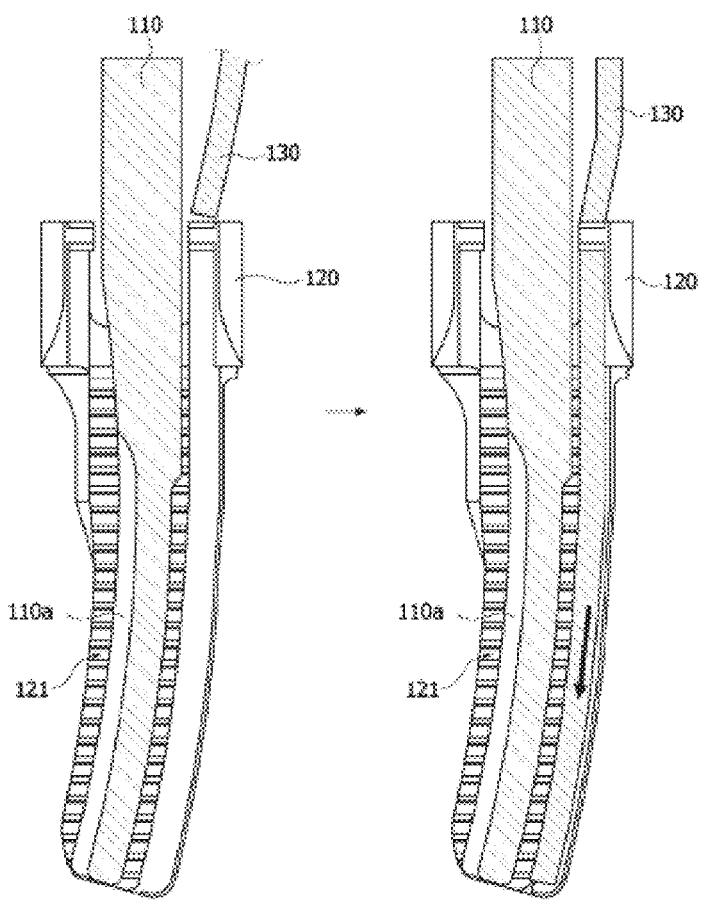

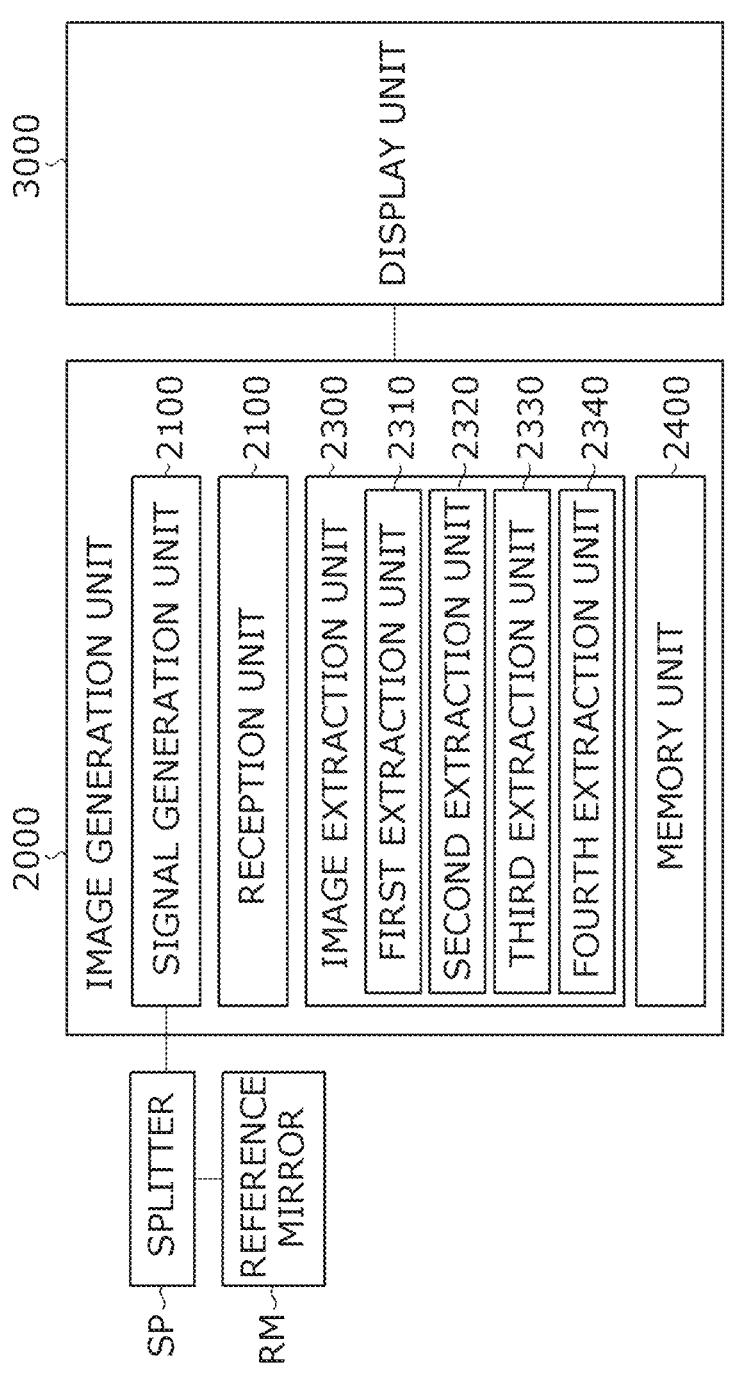
[FIG.28]

[FIG.29]
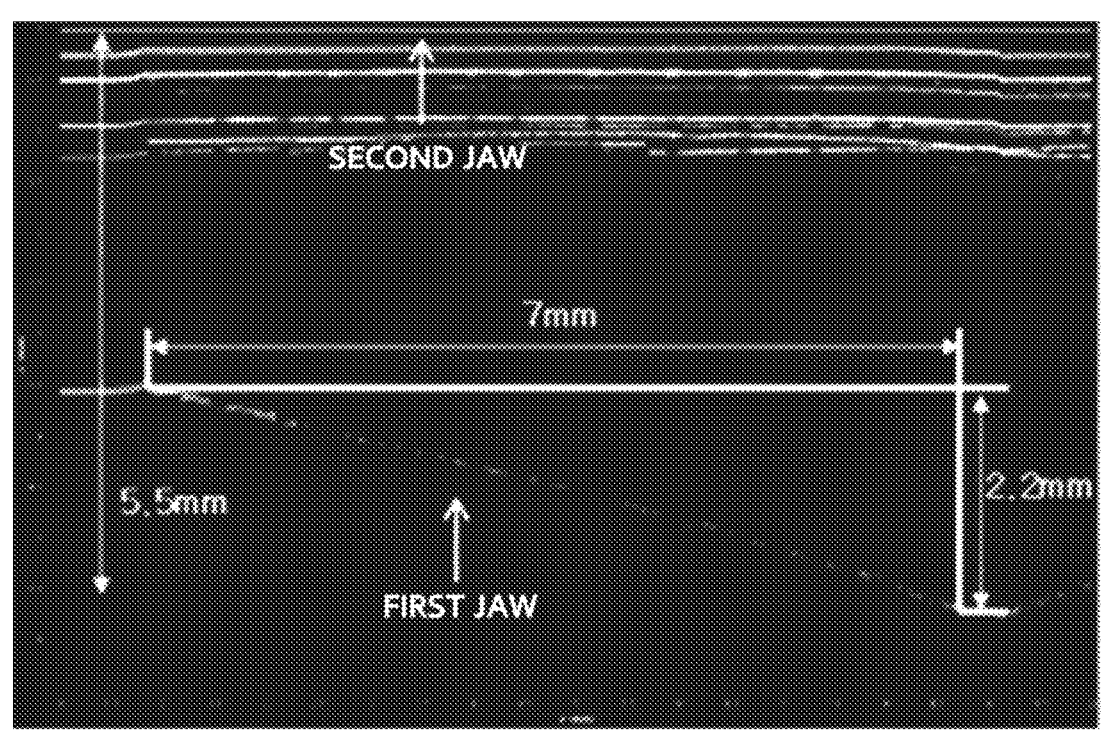

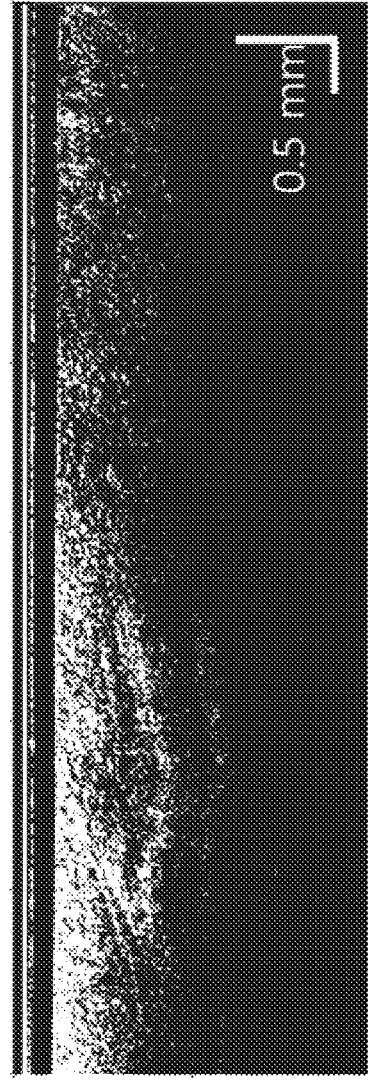
[FIG.30]

[FIG.31]
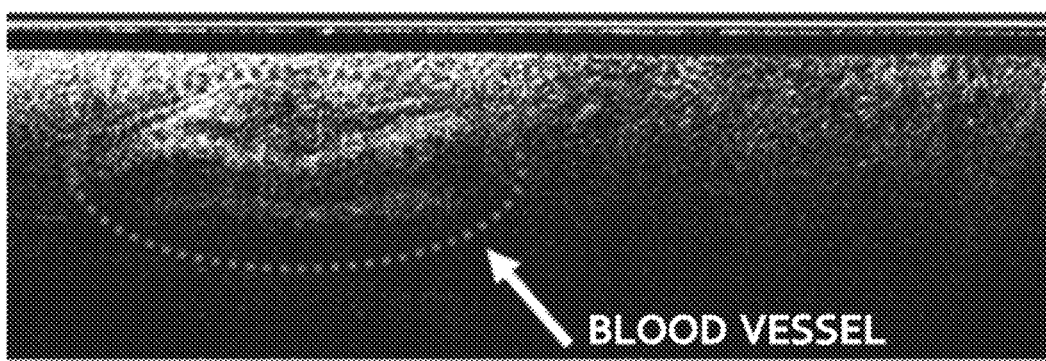
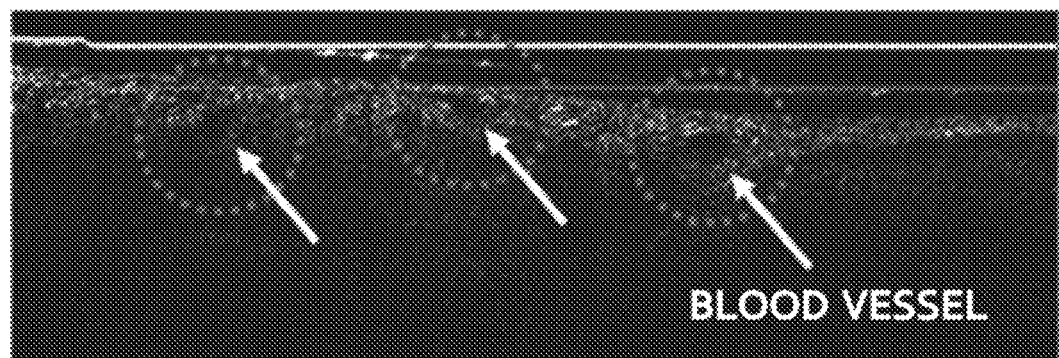

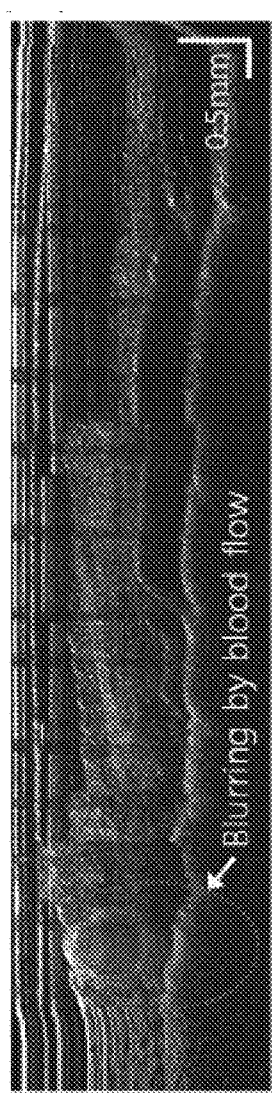
[FIG.32]

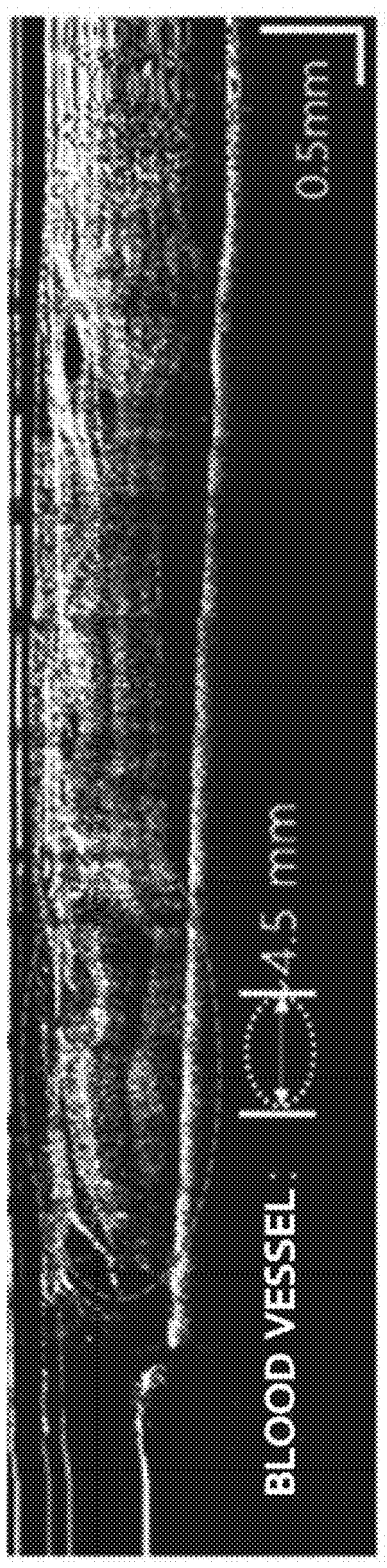
[FIG.33]

TISSUE ABLATION DEVICE, IMAGE GENERATION MODULE, AND TISSUE ABLATION SYSTEM COMPRISING SAME

RELATED APPLICATIONS

This application is a National Phase of PCT Patent Application No. PCT/KR2020/015113 having International filing date of Nov. 2, 2020, which claims the benefit of priority of Korean Patent Application Nos. 10-2019-0164738 filed on Dec. 11, 2019, 10-2019-0164737 filed on Dec. 11, 2019 and 10-2019-0139548 filed on Nov. 4, 2019. The contents of the above applications are all incorporated by reference as if fully set forth herein in their entirety.

FIELD AND BACKGROUND OF THE INVENTION

An embodiment relates to a tissue ablation device, an image generation module, and a system including the same.

Medically, surgery refers to the treatment of diseases by cutting, slitting, or manipulating the skin, mucous membranes, or other tissues using a medical machine. Among these surgical operations, open surgery is an operation in which the skin of an abdominal cavity or face is split open and internal organs, etc., are treated, molded, or removed.

When such open surgery is performed, the skin is cut to form a predetermined space between the skin and the tissue, and then the surgical action is performed through the space, resulting in a lot of scars and slow healing after surgery, such that laparoscopic surgery has recently been attracting attention as an alternative to the open surgery.

Laparoscopic surgery involves making a small hole in a patient's surgical area and inserting a laparoscope through this hole to perform surgery while observing the surgical area in the abdominal cavity, and has been widely used in various internal medicine and surgical operations, urology, obstetrics and gynecology, etc. Due to many advantages over conventional open surgery, such as the shorter recovery period, small scars, reduced pain and risk of infection, etc., laparoscopic surgery has been rapidly developed since cholecystectomy in 1990.

Laparoscopic surgery is currently applied to almost all surgical fields such as colorectal cancer surgery, gastric cancer surgery, hernia, liver resection, thyroid surgery, etc., occupies about 20%-40% of all surgical operations, and is expected to reach 80% of all surgical operations in the future.

Laparoscope is one of the equipment for image diagnosis of internal organs of the body, and is generally configured to observe image information detected from a small camera through a monitor installed outside based on insertion of a device having the small camera mounted thereon into the body.

The location and size of blood vessels inside the tissue to be ablated vary greatly depending on a patient, and information about the location and size is also unknown, such that laparoscopic surgery should be performed by estimating the location of the blood vessels such as arteries, etc., through the doctor's anatomical knowledge and experience, resulting in a high possibility of unintentional vascular resection during tissue ablation.

Resection of the blood vessel during laparoscopic surgery may be such a fatal problem that a considerable amount of time and effort are needed to stop bleeding, which may worsen the conditions of the patient and the doctor, and in the worst case, the patient may die of massive bleeding.

Various studies are being conducted to solve this problem, but they are merely half measures to reduce a problem by stopping the bleeding with energy such as ultrasounds, etc., after vascular resection rather than studies for preventing unintentional vascular resection in laparoscopic tissue ablation.

Moreover, the location of blood vessels passing inside tissues differs from patient to patient, and the size of the blood vessels also varies greatly, the intensity information of an optical signal passing through the tissue may not accurately represent the existence/absence of blood vessels inside the tissue and malfunction of a device may cause a significant risk to the patient during surgery. During the actual surgery, a probability of unintentional vascular resection is about 3%, out of which a probability of a fatal damage is about 18%, and several billions of dollars are spent as treatment costs due to unintentional vascular resection.

Accordingly, a tissue ablation device such as laparoscopy, etc., needs to easily detect blood vessels, etc., in a tissue.

SUMMARY OF THE INVENTION

An embodiment provides a tissue ablation device which easily detects blood vessels, etc., inside a tissue to be ablated.

Moreover, a tissue ablation device is provided in which for accurate ablation, an optical fiber is placed on one side to provide internal imaging using a naked eye or an optical signal.

An embodiment provides a tissue ablation device which easily detects blood vessels, etc., inside a tissue to be ablated.

Moreover, a tissue ablation device is provided in which for accurate ablation, an optical fiber is placed on one side to provide internal imaging using a naked eye or an optical signal.

In addition, a tissue ablation device is provided through which an operator may easily perform ablation and line scanning.

An embodiment provides a tissue ablation device which easily detects blood vessels, etc., inside a tissue to be ablated, an image generation module, and a system including the same.

Furthermore, a tissue ablation device which provides various information referred to in ablation to an operator using scanning, an image generation module, and a system including the same are provided.

Moreover, a tissue ablation device in which for accurate ablation, an optical fiber is placed on one side to provide internal imaging using a naked eye or an optical signal, an image generation module, and a system including the same are provided.

In addition, a tissue ablation device through which an operator may easily perform ablation and line scanning, an image generation module, and a system including the same are provided.

A tissue ablation device is also provided which prevents a damage caused by unintentional vascular resection in various types of surgery, such as laparoscopic surgery, thoracoscopic surgery, robotic surgery, laparotomy, etc.

Problems to be solved in embodiments are not limited thereto, and may include objects or effects that may be understood from solutions to the problems or embodiments described below.

An ablation device according to an embodiment of the present disclosure includes a first jaw, a second jaw including an ablation unit including a protrusion for ablating a tissue and being rotatable with respect to the first jaw under the first jaw, and a signal unit configured to provide a signal to the tissue and receive a reflected signal and disposed on the second jaw, in which the signal unit moves in a longitudinal direction of the ablation unit, the first jaw does not overlap the signal unit in a vertical direction, and the second jaw overlaps the signal unit in the vertical direction.

The second jaw may include a recess in which the ablation unit is nested and a protrusion unit located on a side thereof, and the signal unit may be disposed on the protrusion unit.

The signal unit may include a first signal region overlapping the protrusion unit in the vertical direction and a second signal region overlapping the ablation unit in the vertical direction.

The first jaw may include a first region overlapping the ablation unit in the vertical direction, and an outer surface of the first jaw may have a first curvature in the first region.

An outer surface of the second jaw may have a second curvature in a lower portion of the first region, and an outer surface of the signal unit may have a third curvature in a lower portion of the first region.

The first curvature, the second curvature, and the third curvature may be equal to one another.

The first jaw may include a first outer surface and a second outer surface which extend in the longitudinal direction and face each other, the second jaw may include a first edge surface and a second edge surface which extend in the longitudinal direction and face each other, a first separation distance between the first outer surface and the first edge surface may be less than a second separation distance between the second outer surface and the second edge surface, and the signal unit may be disposed between the second outer surface and the second edge surface.

The signal unit may move in the longitudinal direction between both end portions of the ablation unit.

The signal unit may include a transfer unit through which the signal moves and a transceiving unit configured to emit the signal moving from the transfer unit to the tissue and receive the reflected signal.

The transceiving unit may include a mirror reflecting the signal toward the tissue and a lens unit emitting the tissue reflected from the mirror toward the tissue.

The signal unit may further include a reflection member located in an end portion thereof apart from the transfer unit and the transceiving unit, and the reflection member may reflect the signal emitted from the transceiving unit to the tissue.

The signal unit may include a first signal unit and a second signal unit that are provided in plural, and the first signal unit and the second signal unit may move in the longitudinal direction in different ranges with respect to the tissue.

The first signal unit may be disposed between the second signal unit and the first jaw, and a length of the first signal unit in the longitudinal direction may be less than a length of the second signal unit in the longitudinal direction.

A tissue ablation device according to an embodiment includes an ablation device configured to ablate a tissue, an extension unit connected to the ablation device, a manipulation member configured to manipulate an operation of the ablation device, a first jaw, a second jaw including an ablation unit including a protrusion for ablating a tissue and being rotatable with respect to the first jaw under the first jaw, and a signal unit configured to provide a signal to the tissue and receive a reflected signal and disposed on the second jaw, in which the signal unit moves in a longitudinal direction of the ablation unit, the first jaw does not overlap the signal unit in a vertical direction, and the second jaw overlaps the signal unit in the vertical direction.

A tissue ablation system according to an embodiment includes a tissue ablation device including an ablation device configured to ablate a tissue, an image generation unit configured to provide a signal to the tissue ablation device, receive a signal reflected from the tissue, and output an image signal, and a display unit configured to receive and display the image signal, in which the ablation device includes a first jaw, a second jaw including an ablation unit including a protrusion for ablating a tissue and being rotatable with respect to the first jaw under the first jaw, and a signal unit configured to provide a signal to the tissue and receive a reflected signal and disposed on the second jaw, in which the signal unit moves in a longitudinal direction of the ablation unit, the first jaw does not overlap the signal unit in a vertical direction, and the second jaw overlaps the signal unit in the vertical direction.

A tissue ablation device according to an embodiment of the present disclosure includes an ablation device configured to ablate a tissue, an extension unit connected to the ablation device, a manipulation unit configured to manipulate an operation of the ablation device, and a signal unit disposed to extend along the ablation device, the extension unit, and the manipulation unit, in which the manipulation unit controls opening/closing of the ablation device and moves distally to the ablation device to allow the signal unit to scan the tissue when the ablation device is closed.

The manipulation unit may include a hand holder including an accommodating unit, an opening/closing trigger coupled to the hand holder to switch opening/closing of the ablation device, a scanning trigger configured to switch to allow the signal unit to move distally, and a signal unit movement member connected to the signal unit to move the signal unit toward a distal end portion of the ablation device along with movement of the scanning trigger.

The opening/closing trigger may include a base disposed on an outer side of the hand holder, a first pressing member extending into the opening/closing trigger on a proximal surface of the base, and a second pressing member extending into the opening/closing trigger on the proximal surface of the base.

The first pressing member and the second pressing member may move proximally or distally in the hand holder.

The first pressing member may be connected to the ablation device and the ablation device may be closed in proximal movement.

The tissue ablation device may further include a signal unit holder configured to press or depress the signal unit movement member.

The signal unit holder may press the signal unit movement member when the second pressing member moves distally, and may depress the signal unit movement member when the second pressing member moves proximally.

The first pressing member and the second pressing member may move in the same direction.

The ablation device according to an embodiment of the present disclosure includes a first jaw and a second jaw including an ablation unit including a protrusion for ablating a tissue and being rotatable with respect to the first jaw under the first jaw, and the signal unit may provide a signal to the tissue and receive a reflected signal and disposed on the second jaw, in which the signal unit moves in a longitudinal direction of the ablation unit, the first jaw does not overlap the signal unit in a vertical direction, and the second jaw overlaps the signal unit in the vertical direction.

A tissue ablation system according to an embodiment of the present disclosure includes a tissue ablation device including an ablation device configured to ablate a tissue, an image generation unit configured to provide a signal to the tissue ablation device, receive a signal reflected from the tissue, and output an image signal, and a display unit configured to receive and display the image signal, in which the tissue ablation device includes the ablation device configured to ablate the tissue, an extension unit connected to the ablation device, a manipulation unit configured to manipulate an operation of the ablation device, and a signal unit disposed to extend along the ablation device, the extension unit, and the manipulation unit, in which the manipulation unit controls opening/closing of the ablation device and moves distally to the ablation device to allow the signal unit to scan the tissue when the ablation device is closed.

The image generation module according to an embodiment of the present disclosure may include a signal generation unit configured to generate a signal to be irradiated from the tissue ablation device configured to ablate a tissue to the tissue, a reception unit configured to receive a signal reflected from the tissue, and an image extraction unit configured to output an image signal to which at least one of a location of a blood vessel in the tissue, a speed of blood in the location of the blood vessel, a type of the blood, locations of a lymphatic vessel and a nerve other than the blood vessel, energy for ablating the tissue, and whether to capture the tissue is applied using the reflected signal.

The tissue ablation device may include the ablation device including a first jaw and a second jaw rotationally moving on the first jaw to ablate the tissue, an extension unit connected to the ablation device, a manipulation unit configured to manipulate an operation of the ablation device, and a signal unit disposed to extend along the ablation device, the extension unit, and the manipulation unit and to which a signal generated by the signal generation unit is irradiated, in which the image extraction unit includes a first extraction unit calculates a vertical length and a horizontal length from the image signal by using a minimum separation distance between the first jaw and the second jaw and a length of the first jaw or a length of the second jaw.

The image extraction unit may include a second extraction unit configured to extract a strength of the reflected signal and a region where a blur occurs as a location of the blood vessel.

The second extraction unit may calculate the speed of the blood through the amount of change in the blur.

The second extraction unit may compare the speed of the blood with a preset value and extract a type of the blood as an artery or a vein.

The second extraction unit may extract a size of the blood vessel and control the tissue ablation device when the size of the blood vessel is greater than or equal to a predetermined size.

The second extraction unit may determine whether the second extraction unit overlaps an ablation unit in the tissue ablation device to extract whether the tissue is captured.

A third extraction unit configured to the location of the blood vessel as the location of the lymphatic vessel when the speed of the blood is lower than a preset speed, the location of the blood vessel may be further included.

A fourth extraction unit configured to extract energy irradiated to ablate the tissue from the size of the blood vessel may be further included.

A tissue ablation system according to an embodiment includes a tissue ablation device including an ablation device configured to ablate a tissue, an image generation unit configured to provide a signal to the tissue ablation device, receive a signal reflected from the tissue, and output an image signal, and a display unit configured to receive and display the image signal, in which the image generation unit includes a signal generation unit configured to generate a signal to be irradiated through the tissue ablation device configured to ablate a tissue to the tissue, a reception unit configured to receive a signal reflected from the tissue, and an image extraction unit configured to output an image signal to which at least one of a location of a blood vessel in the tissue, a speed of blood in the location of the blood vessel, a type of the blood, locations of a lymphatic vessel and a nerve other than the blood vessel, energy for ablating the tissue, and whether to capture the tissue is applied using the reflected signal.

An embodiment may implement a tissue ablation device which easily detects blood vessels, etc., inside a tissue to be ablated.

Moreover, a tissue ablation device may be manufactured in which for accurate ablation, an optical fiber is placed on one side to provide internal imaging using a naked eye or an optical signal.

A tissue ablation device may also be manufactured which prevents a damage caused by unintentional vascular resection in various types of surgery, such as laparoscopic surgery, thoracoscopic surgery, robotic surgery, laparotomy, etc.

Various and useful advantages and effects of the present invention are not limited to the foregoing description, and may be more easily understood in a process of describing detailed embodiments of the present invention.

BRIEF DESCRIPTION OF THE SEVERAL
VIEWS OF THE DRAWINGS

FIG. 1 is a block diagram of a tissue ablation system according to an embodiment, FIG. 2 is a conceptual diagram of a tissue ablation device according to an embodiment, FIG. 3 is a perspective view of an ablation device according to a first embodiment, FIG. 4 is an exploded perspective view of the ablation device according to the first embodiment, FIG. 5 is a top view of the ablation device according to the first embodiment, FIG. 6 is a side cross-sectional view of the ablation device according to the first embodiment, FIG. 7 is a side cross-sectional view viewed in a direction different from FIG. 6, FIG. 8 is a front view of the ablation device according to the first embodiment, FIG. 9 is a top view and a bottom view of a first jaw, FIGS. 10 and 11 are views for describing an operation of a signal transfer member, FIG. 12 is a top view of an ablation device according to a second embodiment, FIG. 13 is an enlarged view of a portion A in FIG. 11, FIG. 14 is a top view of an ablation device according to a third embodiment, FIG. 15 is an enlarged view of a portion B in FIG. 14, FIG. 16 is a top view of an ablation device according to a fourth embodiment, FIG. 17 is an enlarged view of a portion C in FIG. 16, FIG. 16 is a conceptual diagram of a tissue ablation device according to an embodiment,

FIG. 17 is a block diagram of a tissue ablation system according to an embodiment, FIG. 18 is a perspective view of the tissue ablation device according to an embodiment, FIG. 19 is a side view of the tissue ablation device according to an embodiment, FIG. 20 is a view for describing a first operation of a manipulation unit and an operation of an ablation device corresponding to the first operation, according to an embodiment, FIG. 21 is a cross-sectional view of a manipulation unit in FIG. 20, FIG. 22 is a view for describing a second operation of the manipulation unit and an operation of the ablation device corresponding to the second operation, according to an embodiment, FIG. 23 is a cross-sectional view of the manipulation unit in FIG. 22, FIG. 24 is a view of a tissue ablation device for describing a third operation of the manipulation unit, according to an embodiment, FIG. 25 is a view for describing a third operation of the manipulation unit according to an embodiment, FIG. 26 is a view for describing an operation of the ablation device corresponding to the third operation, according to an embodiment, FIG. 27 is a view for describing an operation of the ablation device corresponding to the third operation, according to an embodiment, FIG. 28 is a block diagram of an image generation unit and a display unit, according to an embodiment, and FIGS. 29 to 33 are views for describing operations of an image generation unit and a display unit according to an embodiment.

DESCRIPTION OF SPECIFIC EMBODIMENTS OF THE INVENTION

Various changes may be made to the present invention and the present invention may have various embodiments which will be illustrated in the drawings and described in detail in the detailed description. However, such a description is not construed as limited to specified embodiments, and include all changes, equivalents, or substitutes included in the spirit and technical scope of the present invention.

Although ordinal numbers such as "first", "second", and so forth will be used to describe various components of the present invention, those components are not limited by the terms. These terms may be used for the purpose of distinguishing one component from another component. For example, a second component may also be named as a first component without departing from the right scope of the present invention, and similarly, the first component may also be named as the second component. The term "and/or" used herein includes any and all combinations of one or more of the associated listed items.

When a component is referred to as being "connected" or "accessed" to or by any other component, it should be understood that the component may be directly connected or accessed by the other component, but another new component may also be interposed between them. Contrarily, when a component is referred to as being "directly connected" or "directly joined" to or by any other component, it should be understood that there is no component between the component and the other component.

The terms used in the present application are for the purpose of describing particular exemplary embodiments only and are not intended to be limiting. Singular forms include plural forms unless apparently indicated otherwise contextually. It will be further understood that the terms "comprises" and/or "has," when used in this application, specify the presence of a stated feature, number, step, operation, component, element, or combination thereof, but do not preclude the presence or addition of one or more other features, numbers, steps, operations, components, elements, or combinations thereof.

All of the terms used herein including technical or scientific terms have the same meanings as those generally understood by an ordinary skilled person in the related art unless they are defined other. The terms defined in a generally used dictionary should be interpreted as having meanings that are the same as or similar with the contextual meanings of the relevant technology and should not be interpreted as having ideal or exaggerated meanings unless they are clearly defined in the embodiments.

Hereinafter, an embodiment will be described in detail with reference to the accompanying drawings, and regardless of figure symbols, the same component or corresponding components will be given the same reference numeral and a redundant description will not be provided.

FIG. 1 is a block diagram of a tissue ablation system according to an embodiment, and FIG. 2 is a conceptual diagram of a tissue ablation system according to an embodiment.

Referring to FIGS. 1 and 2, a tissue ablation device 1000 according to an embodiment may include an ablation device 100, an extension unit 200, and a manipulation unit 300.

The ablation device 100, which is a device for ablating a desired part of a tissue, may include a first jaw 110, a second jaw 120, and a signal unit 130. This will be described later.

The extension unit 200 may be connected to the ablation device 100. In particular, the extension unit 200 may have a flexibly movable tubular structure. The extension unit 200 may connect the ablation device 100 inserted into the body to an externally installed image generation unit. In the extension unit 200, a connection device, etc., may be disposed such that the signal unit is movable.

The manipulation unit 300 may manipulate an operation of the ablation device 100. For example, the manipulation unit 300 may manipulate rotation of a first jaw and a second jaw by means of the ablation device 100 to perform opening and closing (or opening/closing), thus ablating a tissue. The manipulation unit 300 may also manipulate the signal unit 130 to move in a longitudinal direction (in a distal or proximal direction) for line scanning of the signal unit 130.

For example, the manipulation unit 300 may function using an automatic manipulation method or a manual manipulation method. The automatic manipulation method may be a method in which when there is an input through the manipulation unit 300 (e.g., a push of a button), the signal unit is moved back and forth a predetermined number of times for a predetermined time.

The manual manipulation method may be a method in which an operator manually adjusts all of a speed, a time, etc., of forward movement or backward movement of the manipulation unit 300. Thus, the operator may adjust a scanning distance of a tissue, etc., as desired.

A tissue ablation system according to an embodiment may include a tissue ablation device 1000, an image generation unit 2000, and a display unit 3000.

In an embodiment, the tissue ablation system may insert a front end of the tissue ablation device 1000 into a human body to image the tissue ablation device 1000 such that an ablation area that is an abnormal tissue is distinguishable from a non-ablation area that is a normal tissue in a tissue held in the ablation device of the tissue ablation device 1000.

The tissue ablation device 1000 may have the above-described structure and function, and will not be described below.

The image generation unit 2000 may include a signal generation unit (not shown) and an image signal calculation unit. The signal generation unit (not shown) may be a member that provides a signal to the signal unit of the tissue ablation device.

As the signal generation unit, various light sources for emitting an optical signal, etc., may be applied.

The image signal calculation unit may output an image signal through interference of a signal reflected from the tissue, and transmit the output image signal to the display unit 3000. Herein, the image signal may be a signal obtained by optically interfering with a signal reflected from a surface of a tissue held in an ablation unit provided through the signal unit.

Herein, the interfered signal may be the above-described scan signal that may be an element (e.g., a slope) of a graph calculated by taking a depth at which the optical signal is reflected from the tissue, as an x axis and a backscattered intensity as a y axis. For example, the operator may perform ablation by easily determining a portion with a rapid change in the slope as an ablation tissue and a portion with a gentle change in the slope as a non-ablation tissue, such that the tissue ablation system according to an embodiment may improve the convenience and accuracy of surgery.

Moreover, the image signal calculation unit may include an optical interference optical system to which for example, an optical coherence tomography (OCT) technique is applied for an optical signal.

The display unit 3000 may be connected to the image generation unit 2000 to image a signal (e.g., the optically interfered signal) output from the image generation unit 2000. In this case, the display unit 3000 may image the signal into an ablation area and a non-ablation area of the tissue and provide them to the operator.

At this time, as described above, since the signal unit is disposed on a side surface of the first jaw, the operator may check a location of an ablation tissue on a side surface with the naked eye, and at the same time, check existence/absence of a blood vessel, etc., inside the tissue, thus being able to make a right decision on ablation. Consequently, an accident such as unintentional vascular resection, etc., may be prevented. Moreover, the tissue ablation system according to an embodiment may provide an image enabling the ablation area/the non-ablation area to be easily distinguished without a photographing device such as a camera, etc.

Moreover, it would be understood that various types of components used to ablate microtissues such as blood vessels in various surgical operations such as laparoscopic surgery, thoracoscopic surgery, or robotic surgery, in addition to an ultrasonic or radiofrequency ablation device, may be mounted on the ablation device, within the scope apparent from the standpoint of those of ordinary skill in the art.

FIG. 3 is a perspective view of the ablation device according to the first embodiment, and FIG. 4 is an exploded perspective view of the ablation device according to the first embodiment.

Referring to FIGS. 3 and 4, the tissue ablation device 100 according to the first embodiment may include the first jaw 110, the second jaw 120, and the signal unit 130.

First, the first jaw 110 may extend in a first direction (an X-axis direction). Herein, the first direction (the X-axis direction) as an extension direction of the first jaw 110 may be the same as an extension line of the signal unit 130 described below, and hereinafter will be used interchangeably with a 'longitudinal direction'. A second direction (a Y-axis direction) may be perpendicular to the first direction (the X-axis direction). The second direction (the Y-axis direction) may be a direction from the first jaw toward the signal unit. A third direction (a Z-axis direction) may be perpendicular to the first direction (the X-axis direction) and the second direction (the Y-axis direction). In an embodiment, the third direction (the Z-axis direction) may correspond to a direction from the second jaw toward the first jaw, and may be used interchangeably with a 'vertical direction'.

The first jaw 110 may be located on an upper portion of the ablation device 100. The first jaw 110 may have a curvature in a partial region thereof. In particular, the first jaw 110 may have a curvature in a first region described below. This will be described in detail later.

The first jaw 110 may also have a groove 110a on a side thereof. With this structure, view of a tissue located under the first jaw 110 may be easily secured. The first jaw 110 may ablate and seal a tissue located between the first jaw 110 and the second jaw 120 while moving forward and backward in the first direction (the X-axis direction). The second jaw 120 may be connected to a tube or a pipe, etc., at a rear end of the first jaw 110 to pivot. However, a structure of the tube or the pipe coupled to the second jaw 120 to pivot will be omitted, and various members may be disposed for pivoting and coupling.

The second jaw 120 may be located under the first jaw 110. The second jaw 120 may be coupled to the first jaw 110. In an embodiment, the first jaw 110 or the second jaw 120 may rotationally move. Through the foregoing rotational movement, the first jaw 110 and the second jaw 120 may hold a tissue that may be located between the first jaw 110 and the second jaw 120. The first jaw 110 and the second jaw 120 may easily ablate the tissue at a desired location by means of a protrusion 121a of the second jaw 120. Manipulation for performing ablation may be performed by a manipulation member described below and will be described later.

The second jaw 120 may include a recess RS1 and an ablation unit 121 nested in the recess RS1.

The ablation unit 121 may include the protrusion 121a on an upper portion thereof facing the first jaw 110. In the absence of a tissue between the first jaw 110 and the second jaw 120, the first jaw 110 may contact the protrusion 121a through rotation of the first jaw 110. In an embodiment, the protrusion 121a, when being in a shape protruding upwardly, may be provided in plural.

The ablation unit 121 may also include a sliding unit 121b protruding downwardly. The sliding unit 121b may be nested in the recess RS1. With this structure, the ablation unit 121 may be slidably coupled to the second jaw 120 within the second jaw 120, thus improving a coupling force therebetween.

The recess RS1 may include a sliding groove RS1a that is a groove that may be coupled to the sliding unit 121b. Thus, the sliding unit 121b of the ablation unit 121 may slide into the recess RS1 along the sliding groove RS1a. Subsequently, separation and coupling of the ablation unit 121 may be facilitated, and cleaning may be performed in separation.

The recess RS1 may be formed from a portion to an end surface 120k of the second jaw 120. That is, the recess RS1 may be formed extending in the extension direction of the first jaw 110. The recess RS1 may correspond to a shape of the ablation unit 121.

The recess RS1 may be located on a side of the second jaw 120, and a protrusion unit 120a may be located on the other side of the second jaw 120 by the recess RS1. Thus, both the recess RS1 and the protrusion unit 120a may extend in the longitudinal direction.

More specifically, the second jaw 120 may include the protrusion unit 120a located on a side thereof. The protrusion unit 120a may be adjacent to the recess RS1. The signal unit 130 described below may be disposed on the protrusion unit 120a. That is, the signal unit 130 may be disposed on the second jaw 120. Thus, the signal unit 130 may be disposed apart from the ablation unit 121. With this structure, the ablation device 100 according to an embodiment may easily prevent the signal unit 130 from being damaged by the ablation unit 121.

The signal unit 130 may move in the extension direction (or the longitudinal direction) of the ablation unit 121, e.g., the first direction (the X-axis direction). The signal unit 130 may irradiate a signal (e.g., an optical signal, which will be hereinafter used interchangeably with terms such as an optical signal, light, etc.), toward a tissue held by the first jaw 110 and the second jaw 120. That is, the signal unit 130 may perform line scanning of providing the optical signal for the tissue and receiving a reflected optical signal. The image generation unit described below may then provide an ablation area or a non-ablation area of the tissue as an image by using the optical signal reflected through line scanning.

Forward and backward movement of the signal unit 130 may be adjusted in the longitudinal direction by the manipulation member described below. For example, the manipulation member described below may automatically or manually adjust forward and backward movement of the signal unit.

The signal unit 130 may not overlap the first jaw 110 in the third direction (the Z-axis direction), e.g., the vertical direction. Since the signal unit 130 is nested on the protrusion unit 120a of the second jaw 120, the signal unit 130 may overlap the second jaw 120 in the vertical direction. That is, the signal unit 130 may be supported by the second jaw 120 thereunder. Moreover, the signal unit 130 may be apart from the first jaw 110 on the second jaw 120 in the second direction to irradiate an optical signal to a right location of a tissue to be placed on the second jaw 120. Moreover, line scanning is performed with respect to an entire thickness (a length in the second direction) of the tissue on the second jaw 120 in the longitudinal direction, such that the operator may accurately determine the ablation area and the non-ablation area of the tissue.

The signal unit 130 may include an optical fiber through which the optical signal may be irradiated toward the tissue. Additionally, the signal unit 130 may further include a cover, a buffer, etc., surrounding the optical fiber.

The signal unit 130 may also include both a light irradiation unit and a light reception unit, as described above. The signal unit 130 may include an open transceiving unit 131 at an end portion thereof, and may emit the optical signal and receive the reflected optical signal through the transceiving unit 131. In an embodiment, the light irradiation unit for emitting the optical signal toward the tissue and the light reception unit for receiving the optical signal reflected from the tissue of the signal unit 130 may be connected to the image generation unit. The transceiving unit 131 may be disposed toward the tissue. That is, the transceiving unit 131 may have a shape opened toward a region between the first jaw 110 and the second jaw 120.

The signal unit 130 may be formed of a flexible material to provide a desired shape.

FIG. 5 is a top view of the ablation device according to the first embodiment, FIG. 6 is a side cross-sectional view of the ablation device according to the first embodiment, and FIG. 7 is a side cross-sectional view viewed from a direction that is different from FIG. 6.

Referring to FIGS. 5 to 7, in an embodiment, the first jaw 110 may include a first region S1 and a second region S2. The first region S1 may overlap the ablation unit 121 of the second jaw 120 in the third direction (the Z-axis direction). That is, the first region S1 may be a region in which the first jaw 110 contacts the protrusion 121a of the ablation unit 121 through rotation of the first jaw 110 or the second jaw 120.

The first region S1 may have a first curvature r1 in a partial area or an entire area thereof. In an embodiment, the first jaw 110 may include a first outer surface F1 and a second outer surface F2 which extend in the longitudinal direction and face each other. The first outer surface F1 and the second outer surface F2 may have the first curvature r1. Consequently, the view of the tissue may be easily secured in tissue ablation, and a surrounding organ, etc., may be prevented from being damaged by the first jaw 110.

Correspondingly, the ablation unit 121 of the second jaw 120 may also have a second curvature r2. The first curvature r1 may be equal to the second curvature r2. Hence, a contact area between the first jaw 110 and the ablation unit 121 may have a separation distance of the same ratio with respect to the first jaw 110 and the ablation unit 121 in the second direction. With this structure, a force applied between the first jaw 110 and the ablation unit 121 in contact (e.g., ablation) between the first jaw 110 and the ablation unit 121 may not be concentrated on a side surface. Thus, the reliability of the first jaw 110 and the ablation unit 121 may be improved.

The signal unit 130 may also have a third curvature r3 in a region corresponding to the first region S1 (e.g., a region overlapping the ablation unit in the second direction). The third curvature r3 may be equal to the first curvature r1 and the second curvature r2. With this structure, even when the optical signal, etc., is emitted toward the first jaw 110 through the signal unit 130, as indicated by SG1, and is reflected from the tissue between the first jaw 110 and the ablation unit 121, as indicated by SG2, an error resulting from a distance may be minimized.

In addition, the second jaw 120 may include a first edge surface E1 and a second edge surface E2 which extend in the longitudinal direction and face each other. The first edge surface E1 may be adjacent to the first outer surface F1, and the second edge surface E2 may be adjacent to the second outer surface F2. That is, the first edge surface E1 may be located corresponding to the groove 110a in the first jaw 110, and the second edge surface E2 may be located in adjacent to the signal unit 130 or the protrusion unit 120a.

In an embodiment, a first separation distance d1 between the first outer surface F1 and the first edge surface E1 may be shorter than a second separation distance d2 between the second outer surface F2 and the second edge surface E2. With this structure, the second jaw 120 may easily form the protrusion unit 120a on a side thereof. Moreover, since the signal unit is located between the second outer surface F2 and the second edge surface E2, it is possible to easily provide a space in which the signal unit 130 may be arranged, by making the second separation distance d2 larger than the first separation distance d1. Moreover, by reducing the first separation distance d1 between the first outer surface F1 and the first edge surface E1, view allowing a location of the tissue located between the first jaw 110 and the second jaw 120, in particular, an ablation location to be accurately recognized may be provided.

Moreover, the groove 110*a* may be disposed on the first outer side surface F1 as described above to provide accurate view of a tissue that is an ablation target.

Moreover, the end surface 120*k* of the second jaw 120 may further extend in the first direction (or the longitudinal direction) than an end portion of the first jaw 110.

FIG. 8 is a front view of the ablation device according to the first embodiment.

Referring to FIG. 8, in the ablation device according to the first embodiment, a maximum height h1 of the ablation unit 121 may be greater than a maximum height of a protrusion unit h2. That is, the signal unit 130 may partially overlap the ablation unit 121 in the second direction (the Y-axis direction). Hence, the tissue located on the ablation unit 121 may be located to overlap the signal unit 130 in the second direction (the Y-axis direction), and thus light emitted through the signal unit 130 may be provided to the tissue. As a result, in emission and reflection of the signal through the signal unit 130, noise of the signal may be reduced, such that the accuracy of detection of a blood vessel, etc., as a tissue ablation device described below may be improved greatly.

The signal unit 130 may also include a first signal region 130-1 overlapping the protrusion unit 120*a* in the third direction (the Z-axis direction) and a second signal region 130-2 overlapping the ablation unit 121 in the third direction (the Z-axis direction).

The first signal region 130-1 may be disposed on the protrusion unit 120*a* to contact the protrusion unit 120*a*. However, the present disclosure is not limited thereto, and a coupling member such as a movement member, etc., may be located between the first signal region 130-1 and the protrusion unit 120*a*.

The second signal region 130-2 may overlap the ablation unit 121 in the third direction (the Z-axis direction) as described above, such that a side of the signal unit 130 may be disposed adjacent to the first jaw 110. A length of the first signal region 130-1 in the second direction may be greater than a length of the second signal region 130-2 in the second direction. Thus, the signal unit 130 may be sufficiently supported on the protrusion unit 120*a*. Moreover, the ablation device according to an embodiment may minimize a separation distance between the signal unit 130 and the first jaw 110 through the second signal region 130-2, thereby minimizing noise of the signal emitted through the signal unit 130.

FIG. 9 illustrates a top view and a bottom view of a first jaw. More specifically, in FIG. 9, (a) is the top view of the first jaw and (b) is the bottom view of the first jaw.

Referring to FIGS. 9(*a*) and 9(*b*), both the first outer surface F1 and the second outer surface F2 may have curvatures. In an embodiment, the first outer surfaces F1 and the second outer surfaces F2 of a bottom surface 110-1 and a top surface 110-2 of the first jaw 110 may have curvatures in at least partial regions thereof. In particular, a first-first curvature r1 of the second outer surface F2 and a first-second curvature r1' of the first outer surface F1 may be equal to each other, and may be located on lower ends of the first outer surface F1 and the second outer surface F2. Thus, the ablation device according to an embodiment may easily check the tissue as described above, and prevent organs adjacent to the tissue from being damaged by the ablation device.

FIGS. 10 and 11 are views for describing an operation of a signal transfer member.

Referring to FIGS. 10 and 11, the signal unit 130 may be disposed apart from the first jaw 110 in the second direction and may be disposed on the second jaw 120 to move in the first direction (the longitudinal direction).

First, the signal unit 130 may include the transceiving unit 131 that emits the signal to the tissue as indicated by SG1 and receives the signal reflected from the tissue as indicated by SG2, and the transceiving unit 131 may be located in an end portion in the longitudinal direction. That is, the transceiving unit 131 may be located on an end portion of the protrusion unit 120*a* of the second jaw 120.

In an embodiment, for line scanning of a human organ, the transceiving unit 131 may be located on an upper end of the ablation unit 121 of the second jaw 120 and may move from the upper end of the ablation unit 121 to a lower end of the ablation unit 121 as indicated by LS. That is, the signal unit 130 or the transceiving unit 131 may move in the longitudinal direction between both end portions of the ablation unit 121.

As the transceiving unit 131 performs line scanning with respect to the tissue, the tissue ablation device described below may image an ablation area and a non-ablation area of the human tissue such as a blood vessel in the line-scanned tissue into a human-recognizable image. Consequently, the ablation device according to an embodiment may provide an image to allow immediate recognition of whether a human tissue held in the ablation device is the ablation region or the non-ablation region in various surgical operations such as laparoscopic surgery, thoracoscopic surgery, robotic surgery, etc., such that a user such as a doctor, etc., may easily ablate only a required region.

FIG. 12 is a top view of an ablation device according to a second embodiment, and FIG. 13 is an enlarged view of a portion A of FIG. 11.

The ablation device according to the second embodiment may include the first jaw 110, the second jaw 120, and a signal unit 230. The same description according to the first embodiment may be equally applied to the first jaw 110 and the second jaw 120. It should be understood that the foregoing description may also be applied to a function (signal transmission/reception) of the signal unit 230 and the following description may be applied with a different structure.

The signal unit 230 may include a transfer unit 231 through which a signal moves and a transceiving unit 232 that emits the signal moved from the transfer unit 231 to a tissue. The foregoing description about the transceiving unit may be applied to the transceiving unit 232. The transceiving unit 232 may include a mirror 233 and a lens unit 234. The mirror 233 may be located on an end of the transfer unit 231 and reflect the signal moved from the transfer unit 231. The lens unit 234 may emit the signal reflected from the mirror 233 toward the tissue.

First, the transfer unit 231 may include an optical fiber and a cover surrounding the optical fiber. The transfer unit 231 may be connected to a manipulation member of the tissue ablation device in a rear end thereof. Moreover, the transfer unit 213 may be connected to the image generation unit described below to provide an image of a blood vessel, etc., of a tissue with the reflected signal. The image generation unit and the manipulation member will be described later.

The transfer unit 231 may include the optical fiber and transmit and receive the signal by moving in the longitudinal direction as described above, thereby performing line scanning on the tissue.

The mirror 233 may reflect the signal transmitted through the transfer unit 231 to the tissue. The mirror 233 may also receive the signal reflected from the tissue and reflect the signal to the transfer unit 231. For example, the mirror 233 may change a path of the signal by perpendicularly reflecting the signal moved through the transfer unit 231 to emit the signal to the tissue. With this structure, line scanning may be performed on a tissue adjacent to the signal unit 130.

In an embodiment, the mirror 233 and the lens unit 234 may be located to face each other. In an embodiment, the lens unit 234 may be located between the mirror 233 and the first jaw 110. In other words, the lens unit 234 may be located in more adjacent to the first jaw 110 than the mirror 233.

The lens unit 234 may have a predetermined curvature shape to project the signal reflected from the mirror 233 to the tissue. For example, the lens unit 234 may collect or diffuse the reflected signal.

FIG. 14 is a top view of an ablation device according to a third embodiment, and FIG. 15 is an enlarged view of a portion B of FIG. 14.

The ablation device according to the third embodiment may include the first jaw 110, the second jaw 120, and a signal unit 130'. The same description according to several embodiments may be equally applied to the first jaw 110 and the second jaw 120. It should be understood that the foregoing description may also be applied to a function (signal transmission/reception) of the signal unit 130' and the following description may be applied with a different structure.

Referring to FIGS. 14 and 15, the signal unit 130' may include a transfer unit 131' through which a signal moves, a transceiving unit 132' that emits the signal moved from the transfer unit 131' to a tissue, and a reflection member 133' that reflects the light emitted from the transceiving unit to the tissue. Likewise, the foregoing description about the transceiving unit may be applied to the transceiving unit 132'.

The transfer unit 131' may include the optical fiber and transmit and receive the signal by moving in the longitudinal direction as described above, thereby performing line scanning on the tissue.

The transceiving unit 132' may diffuse the signal moved through the transfer unit 131'. For example, the transceiving unit 132' may include a lens.

The reflection member 133' may be located under the transfer unit 131' and the transceiving unit 132'. That is, the reflection member 133' may be located at a lowermost portion of the signal unit 130', and may be located in more adjacent to an end surface of the second jaw 120 than the transfer unit 131' and the transceiving unit 132'.

The reflection member 133' may have a surface inclined at a predetermined inclination angle, e.g., 45 degrees. With this structure, the reflection member 133' may reflect the signal emitted through the transceiving unit 132' such that the signal is incident toward the tissue.

FIG. 16 is a top view of an ablation device according to a fourth embodiment, and FIG. 17 is an enlarged view of a portion C of FIG. 16.

The ablation device according to the fourth embodiment may include the first jaw 110, the second jaw 120, and a signal unit 430. The same description according to several embodiments may be equally applied to the first jaw 110 and the second jaw 120. It should be understood that the foregoing description may also be applied to a function (signal transmission/reception) of the signal unit 430 and the following description may be applied with a different structure.

Referring to FIGS. 16 and 17, in the ablation device according to the fourth embodiment, the signal unit 430 may be provided in plural. For example, the signal unit 430 may include a first signal unit 431 and a second signal unit 432. The first signal unit 431 and the second signal unit 432 may perform line scanning on the tissue, like the signal unit described in the ablation device according to the first to third embodiments.

However, the first signal unit 431 may move in the longitudinal direction only within a predetermined range in the first region S1. In addition, the second signal unit 432 may move in the longitudinal direction only within a predetermined range1 in the first region S1.

In this case, the first signal unit 431 and the second signal unit 432 may move in the longitudinal direction in different ranges. In an embodiment, the first signal unit 431 may be located in more adjacent to the first jaw 110 than the second signal unit 432.

Moreover, the first signal unit 431 and the second signal unit 432 have different lengths in the longitudinal direction. In an embodiment, the length of the first signal unit 431 in the longitudinal direction may be less than the length of the second signal unit 432 in the longitudinal direction. Thus, the first signal unit 431 may be located between the second signal unit 432 and the first jaw 110.

The first signal unit 431 may move only in an upper region in the first region S1, as indicated by SLA. On the other hand, the second signal unit 432 may move only in a lower region in the first region S1, as indicated by SLB. With this structure, the first signal unit 431 and the second signal unit 432 may perform line scanning with respect to different regions in the first region S1. With this structure, the ablation device according to the fourth embodiment may perform line scanning on the tissue during a less time.

Additionally, the first signal unit 431 and the second signal unit 432 have the same moving direction or different moving directions. For example, the first signal unit 431 and the second signal unit 432 may move up or down within one identical time range in a predetermined period. For the identical moving direction, a separation distance DL between an end portion of the first signal unit 431 (e.g., a transceiving unit) and an end portion of the second signal unit 432 (e.g., a transceiving unit) may be maintained, such that noise resulting from light emitted through each of the first signal unit 431 and the second signal unit 432 may be maintained identical.

For a different moving direction, noise resulting from the light emitted through each of the first signal unit 431 and the second signal unit 432 may be minimized for some time.

Moreover, it would be understood that various types of components used to ablate microtissues such as blood vessels in various surgical operations such as laparoscopic surgery, thoracoscopic surgery, or robotic surgery, in addition to an ultrasonic or radiofrequency ablation device, may be mounted on the ablation device, within the scope apparent from the standpoint of those of ordinary skill in the art.

FIG. 16 is a conceptual diagram of a tissue ablation device according to an embodiment.

The tissue ablation device 1000 according to an embodiment may include the ablation device 100, the extension unit 200, and the manipulation member 300.

First, it would be understood that the above-described ablation device according to various embodiments may be applied as the ablation device 100.

The extension unit 200 may be connected to the ablation device 100. In particular, the extension unit 200 may have a flexibly movable tubular structure. The extension unit 200 may connect the ablation device 100 inserted into the body to an image generation unit which will be later described and is installed on an outer side. In the extension unit 200, a connection device, etc., may be disposed such that the signal unit is movable.

The manipulation member 300 may manipulate an operation of the ablation device 100. For example, the manipulation member 300 may manipulate rotation of a first jaw and a second jaw by means of the ablation device 100 to ablate a tissue. The manipulation member 300 may also manipulate the signal unit 130 to move in a longitudinal direction for line scanning of the signal unit 130.

For example, the manipulation member 300 may function using an automatic manipulation method or a manual manipulation method. The automatic manipulation method may be a method in which when there is an input through the manipulation member 300 (e.g., a push of a button), the signal unit is moved back and forth a predetermined number of times for a predetermined time.

The manual manipulation method may be a method in which an operator manually adjusts all of a speed, a time, etc., of forward movement or backward movement of the manipulation member 300. Thus, the operator may adjust a scanning distance of a tissue, etc., as desired.

FIG. 17 is a block diagram of a tissue ablation system according to an embodiment.

Referring to FIG. 17, a tissue ablation system according to an embodiment may include the tissue ablation device 1000, the image generation unit 2000, and the display unit 3000.

In an embodiment, the tissue ablation system may insert a front end of the tissue ablation device 1000 into a human body to image the tissue ablation device 1000 such that an ablation area that is an abnormal tissue is distinguishable from a non-ablation area that is a normal tissue in a tissue held in an ablation unit of the tissue ablation device 1000.

The tissue ablation device 1000 may have the above-described structure and function, and will not be described below.

The image generation unit 2000 may include a signal generation unit (not shown) and an image signal calculation unit. The signal generation unit (not shown) may be a member that provides a signal to the signal unit of the tissue ablation device.

As the signal generation unit, various light sources for emitting an optical signal, etc., may be applied.

The image signal calculation unit may output an image signal through interference of a signal reflected from the tissue, and transmit the output image signal to the display unit 3000. Herein, the image signal may be a signal obtained by optically interfering with a signal reflected from a surface of a tissue held in an ablation unit provided through the signal unit.

Herein, the interfered signal may be the above-described scan signal that may be an element (e.g., a slope) of a graph calculated by taking a depth at which the optical signal is reflected from the tissue, as an x axis and a backscattered intensity as a y axis. For example, the operator may perform ablation by easily determining a portion with a rapid change in the slope as an ablation tissue and a portion with a gentle change in the slope as a non-ablation tissue, such that the tissue ablation system according to an embodiment may improve the convenience and accuracy of surgery.

Moreover, the image signal calculation unit may include an optical interference optical system to which for example, an optical coherence tomography (OCT) technique is applied for an optical signal.

The display unit 3000 may be connected to the image generation unit 2000 to image a signal (e.g., the optically interfered signal) output from the image generation unit 2000. In this case, the display unit 3000 may image the signal into an ablation area and a non-ablation area of the tissue and provide them to the operator.

FIG. 18 is a perspective view of the tissue ablation device according to an embodiment, FIG. 19 is a side view of the tissue ablation device according to an embodiment, FIG. 20 is a view for describing a first operation of a manipulation unit and an operation of an ablation device corresponding to the first operation, according to an embodiment, and FIG. 21 is a cross-sectional view of a manipulation unit in FIG. 20.

Referring to FIGS. 18 and 21, the tissue ablation device according to an embodiment may include the ablation device 100, the extension unit 200, and the manipulation unit 300.

The manipulation unit 300 may include a hand holder 310, an opening/closing trigger 320, a scanning trigger 330, a switch unit 340, a signal unit movement member 350, a signal unit holder 360, and a rotation member 370.

First, the hand holder 310 may include a first housing located on a side and a second housing located on the other side, in the first direction. The first housing and the second housing may be coupled in various coupling manners. It would be understood that various components described herein may be coupled in various coupling manners.

The hand holder 310 may be formed in a shape easily holdable by the operator.

The hand holder 310 may also have an accommodating unit therein. In the accommodating unit, various components described below may be disposed. Hereinbelow, it will be described that in the first direction (the X-axis direction), a location closer to the ablation device is distal and the opposite case is proximal.

The hand holder 310 may have a grip anchor or a saddle surface. The saddle surface may be located on a web where the thumb and forefinger are connected on the hand.

Also, a palm-facing proximal surface under the hand holder 310 may have a pistol grip outline portion for receiving the palm of the hand. The proximal surface may be formed to have an outline capable of accommodating the palm of the hand.

The hand holder 310 may include a protrusion unit protruding toward a proximal side on the grip anchor. The protrusion unit may abut against the uppermost finger web of the hand located between the thumb and forefinger to structurally stabilize the hand holder 310 and make it easy for the operator to control the hand holder.

The opening/closing trigger 320 may switch (on/off) opening/closing of the ablation device. The opening/closing trigger 320 may be located under the hand holder 310 and be coupled to the hand holder 310. The opening/closing trigger 320 may be coupled to the hand holder 310 so as to be rotationally driven.

A portion of the opening/closing trigger 320 may be inserted into the hand holder 310 through rotational driving. The opening/closing trigger 320 may be formed ergonomically to facilitate the operator's interfacing. The opening/closing trigger 320, when having a squeezing force of the operator applied thereto, may perform rotational driving of the first jaw and the second jaw as the aforementioned portion is inserted into the hand holder 310. This will be described in detail later.

The opening/closing trigger 320 may include abase 321, a first pressing member 322, and a second pressing member 323.

The base 321 may be a portion which is located outside the hand holder 310 and to which the operator's squeezing force is applied in contact with the operator's finger. The base 321 may perform rotation by the operator's squeezing force. In addition, the base 321 may be formed in a hook shape.

The first pressing member 322 may be connected to the base 321 and extend toward the opening/closing trigger 320 on the proximal surface of the base 321. At least a part of the first pressing member 322 may be located in the hand holder 310. That is, the first pressing member 322 may overlap the hand holder 310 in a direction perpendicular to the first direction.

The first pressing member 322 may move proximally or distally within the hand holder 310. At this time, the first pressing member 322 may be coupled to the hand holder 310 through a hook hk connected to the hand holder 310. In an embodiment, when the first pressing member 322 is maximally moved proximally in the hand holder 310, the hook hk may be coupled to a protrusion to be formed on the first pressing member 322. Thus, the first pressing member 322 may be maintained in a maximally proximally moved state within the hand holder 310. That is, a locking state may be achieved by movement of the first pressing member 322 and the hook hk. In the locking state, movement of the scanning trigger 330 may be possible. This will be described in detail later. Even in the locking state, movement of the first pressing member 322 within a predetermined range may be partially possible.

When the first pressing member 322 moves proximally as indicated by A1, the first jaw and the second jaw are closed by rotation of the first jaw or the second jaw as indicated by B1. In other words, the first jaw and the second jaw may hold a tissue.

On the other hand, when the first pressing member 322 moves distally as indicated by A2, the first jaw and the second jaw are opened by rotation of the first jaw or the second jaw as indicated by B2. In other words, the first jaw and the second jaw may not hold a tissue.

The second pressing member 323 may be located on the first pressing member 322. The second pressing member 323 may be connected to the signal unit movement member 350 through a first connection member LE1. Like the first pressing member 322, the second pressing member 323 may move proximally or distally along with movement of the base 321.

The second pressing member 323 may move proximally or distally inside the hand holder 310. The second pressing member 323 may move proximally within the hand holder 310 by the squeezing force of the operator. In this case, the first connection member LE1 connected to the second pressing member 323 may be moved proximally.

The first connection member LE1 may be coupled to a first elastic member SP1 disposed on a proximal end portion. In an embodiment, when the first connection member LE1 moves proximally or distally by the second pressing member 323, the first connection member LE1 may also move proximally or distally along with the second pressing member 323 to press the first elastic member SP1.

Also, in the locking state, an end portion of the second pressing member 323 is maximally moved proximally, and an end (proximal) portion of the first connection member LE1 may also maximally moved proximally.

The first elastic member SP1 may be compressed or expanded according to movement of the first connection member LE1. Moreover, the other (proximal) end portion of the first connection member LE1 may be moved proximally or distally.

Moreover, the first elastic member SP1 may be a spring.

The scanning trigger 330 may cause the signal unit 130 to move in the first direction (e.g., a distal direction). In an embodiment, when the scanning trigger 330 moves downwardly by manipulation (pressing) of the operator, the signal unit 130 may be moved distally to perform line scanning. On the other hand, in the absence of manipulation of the operator, the scanning trigger 330 may maintain a state of moving upwardly and proximally. In this case, an end portion of the signal unit 130 may be disposed apart from the first jaw or the second jaw in the first direction. That is, this state may be a standby state before scanning with respect to a tissue is performed using the signal unit 130. Movement of the scanning trigger 330 based on the operator's manipulation will be described later.

The switching unit 340 may be located on a side of the hand holder 310. The switching unit 340 may include a plurality of switches. The switching unit 240 may control ablation or rotation of the rotation member 370 in the ablation device.

In an embodiment, when a switch moves from proximally to distally, a blade may move between the first jaw and the second jaw to perform ablation on a tissue in the ablation device. The switch may be connected to the blade in various manners.

When the switch moves from proximally to distally, the rotation member 370 may perform a rotation operation. Thus, the extension unit and the ablation device may rotate. In this way, the operator may rotate the ablation device in an easy direction depending on the direction of the tissue. This will be described in detail later.

The signal unit movement member 350 may be connected to the scanning trigger 330 through the first connection member, the signal unit holder 360, and the second connection member LE2.

When the scanning trigger 330 moves to a side (e.g., a lower portion), the connection member LE2 may move distally and the signal unit movement member 350 may also move distally along with movement of the connection member LE2. Thus, the signal unit holder 360 connected to the signal unit movement member 350 may move distally. In correspondence to the aforementioned distal movement, opposite proximal movement may be performed.

The signal unit movement member 350 may move distally only in a state where the first pressing member 322 and the second pressing member 323 are maximally moved proximally.

In an embodiment, the tissue ablation device may further include a signal unit holder HD for supporting the signal unit movement member 350. One end of the signal unit holder HD may abut against the first connection member LE1 and may be supported by the first connection member LE1. The signal unit holder HD may press or depress the signal unit movement member 350 along proximal or distal movement of the first connection member LE1.

When the second pressing member 323 moves proximally, the first connection member LE1 may also move proximally and the signal unit holder HD supported by the first connection member LE1 may move upwardly. In this case, an end portion (a distal side) of the first connection member LE1 may be structured to extend upwardly.

In a state where the second pressing member 323 moves distally, the signal unit holder HD may press the signal unit movement member 350. In a state where the second pressing member 323 moves proximally, the signal unit holder HD may move upwardly and may not press the signal unit movement member 350. Thus, the signal unit movement member 350 may move distally.

Moreover, the second pressing member 323 may move in the same direction (proximally or distally) as the first pressing member 322. Thus, tissue holding may be performed by an operator's action (e.g., pressing), and then line scanning of the signal unit may become possible.

The signal unit holder 360 may be coupled to an end portion (a distal end portion) of the signal unit movement member 350. The signal unit movement member 350 moves proximally or distally, and in correspondence to this movement, the signal unit holder 360 may move proximally or distally.

The signal unit holder 360 may have the signal unit 130 located therein, and have a holding member with a spiral structure located therein. The holding member may be coupled to the signal unit holder 360 and the signal unit 130. The holding member may move proximally or distally in correspondence to proximal or distal movement of the signal unit holder 360. The signal unit holder 360 may enable line scanning to be accurately performed along with proximal or distal movement of the signal unit 130 by minimizing vibration occurring in movement.

The rotation member 370 may be located in proximity to the signal unit holder 360 and may be coupled to the extension unit. The rotation member 370 may be connected to the switching unit, such that when the operator manipulates the switching unit, the rotation member 370 may rotate in correspondence to the manipulation. In addition, the extension unit and the ablation device coupled thereto may also rotate. Thus, the operator may easily rotate the ablation device in a direction facilitating ablation in correspondence to location and shape of a blood vessel.

Moreover, the manipulation unit 300 may further include a sensor 380.

The sensor 380 may sense a moving distance of the signal unit. In an embodiment, the sensor 380 may be located in the hand holder 310. The sensor 380 may be located on the second connection member LE2 or the signal unit movement member 350 to sense proximal or distal movement of the second connection member LE2 or the signal unit movement member 350.

In an embodiment, the sensor 380 as a potential meter may sense a moving distance of the signal unit 130 through a rotation angle of the second connection member LE2. Alternatively, the sensor 380 may sense a moving distance of the signal unit 130 through a moving distance of the movement member 350.

Hereinbelow, an operation of the manipulation unit will be described based on the foregoing description, and a first operation of the manipulation unit corresponds to a case where the opening/closing trigger 320 is located distally. That is, in the ablation device, the end portions of the first jaw and the second jaw are opened apart from each other. In addition, in the first operation, the signal unit 130 may be maximally apart from a distal end portion of the ablation device, such that line scanning may not be performed. More specifically, the first pressing member 322 and the second pressing member 323 move distally and the first connection member LE1 moves distally such that the signal unit holder HD may press the signal unit movement member 350. Thus, movement of the signal unit movement member 350 is limited, such that manipulation for movement of the signal unit by the scanning trigger 330 may be blocked. Subsequently, the tissue ablation device may improve power efficiency and prevent a damage from occurring due to movement of the signal unit by performing line scanning for ablation only when the tissue is held.

FIG. 22 is a view for describing a second operation of the manipulation unit and an operation of the ablation device corresponding to the second operation, according to an embodiment, and FIG. 23 is a cross-sectional view of the manipulation unit of FIG. 22.

Referring to FIGS. 22 and 23, when the operator presses the opening/closing trigger 320, a second operation of the manipulation unit may be performed. As described above, by pressing of the operator, the end (proximal) portions of the first pressing member 322 and the second pressing member 323 may maximally move proximally.

Through rotation or movement of the opening/closing trigger 320, the first jaw or the second jaw connected to the opening/closing trigger 320 may rotate such that a separation distance between the end portions of the first jaw or the second jaw is reduced and thus the first jaw or the second jaw is closed, as indicated by k0. In other words, the first jaw and the second jaw may hold a tissue therebetween.

In the second operation, through proximal movement of the second pressing member 322, the first connection member LE1 may move proximally while compressing the first elastic member SP1, as indicated by k1. Thus, as a distal end portion located uppermost in the first connection member LE of the first connection member LE1 moves proximally, the distal end portion may abut against the signal unit holder HD. Thus, the signal unit holder HD moves upwardly in correspondence to movement of the first connection member LE1 and pressing of the signal unit movement member 350 may be released, as indicated by k2. Thus, the signal unit movement member 350 may enter a movable state. Accordingly, it is possible to prevent the signal unit from being damaged by rotation of the second jaw, etc., while performing line scanning of the tissue in the held state.

FIG. 24 is a view of a tissue ablation device for describing a third operation of the manipulation unit, according to an embodiment, FIG. 25 is a view for describing a third operation of the manipulation unit according to an embodiment, FIG. 26 is a view for describing an operation of the ablation device corresponding to the third operation, according to an embodiment, and FIG. 27 is a view for describing an operation of the ablation device corresponding to the third operation, according to an embodiment.

Referring to FIGS. 24 to 27, after the second operation, the operator may move the scanning trigger 330. When the operator moves the scanning trigger 330 down as indicated by M0, the second connection member LE2 connected to the scanning trigger 330 may move distally as indicated by M1.

The signal unit movement member 350 connected to the second connection member LE2 may move distally as indicated by M2. Correspondingly, the signal unit holder 360 connected to the signal unit movement member 350 may move distally in a state of holding the signal unit, as indicated by M3. The signal unit 130 may lead into the signal unit holder 360 and move distally to the end portion of the ablation device along the extension unit, as indicated by M4.

In an embodiment, a distally moving distance of the signal unit 130 may be adjusted according to the degree of movement of the scanning trigger 330. Alternatively, in movement of the scanning trigger 330, the signal unit 130 may move distally to the end portion of the ablation device and then move proximally to perform line scanning.

Moreover, like the second operation, a third operation of the manipulation unit may be performed in a state where the first jaw and the second jaw are closed. Thus, the operator may accurately perform line scanning on a tissue by distally or proximally moving the signal unit while holding the tissue. In addition, the third operation is performed in the closed state of the first jaw and the second jaw, such that even after an optical signal emitted through the signal unit transmits a tissue, etc., at least a part of the optical signal may be reflected from the first jaw. As a distance between the first jaw and the signal unit is maintained identical, more accurate scanning may be performed than in a state where the first jaw and the second jaw are opened.

Moreover, holding of the tissue with the first jaw and the second jaw and line scanning through movement of the signal unit may be performed separately. That is, the operator may primarily recognize an ablation area with the naked eye by holding the tissue in ablation device through the first operation and the second operation and secondarily perform line scanning based on the third operation to re-check the ablation area. In addition, the held state of the tissue is maintained before and after line scanning, such that the ablation area is not changed and the first jaw and the signal unit do not overlap in the vertical direction, thereby preventing the tissue from being damaged even when the signal unit performs scanning during holding.

FIG. 28 is a block diagram of an image generation unit and a display unit, according to an embodiment, and FIGS. 29 to 33 are views for describing operations of an image generation unit and a display unit according to an embodiment.

Referring to FIG. 28, the image generation unit 2000 may include a signal generation unit 2100, a reception unit 2200, an image extraction unit 2300, and a memory unit 2400. Moreover, the image generation unit 2000 may further include a splitter SP and a reference mirror RM.

The signal generation unit 2100 may generate a signal to be provided to a tissue along the signal unit to calculate an image. The signal generation unit 2100 may be connected to the signal unit and output the signal to the signal unit.

The signal generation unit 2100 may include a light source that may irradiate a laser beam used for OCT measurement. The light source may include a wavelength tunable laser.

A part (a first signal) of the signal generated in the signal generation unit 2100 may be reflected by the splitter SP and then be irradiated to the reference mirror RM which may reflect the irradiated signal, and the reflected signal, i.e., a reference signal (e.g., reference light) may be provided to the reception unit 2200.

Another part (a second signal) of the signal generated in the signal generation unit 2100 may be irradiated to a target (e.g., a tissue) through the splitter SP along the signal unit, and the signal reflected from the tissue (e.g., a sample signal or sample light) may be provided to the reception unit 2200 along the signal unit.

The splitter SP may separate the generated signal (e.g., into the first signal and the second signal) and change an optical path to irradiate them to the reference mirror RM through refraction. The splitter SP may pass a reference signal reflected from the reference mirror RM therethrough to direct the reference signal toward the reception unit 2200.

The reference mirror RM may reflect a part of the separated signals to generate the reference signal. The splitter SP and the reference mirror RM may be connected to the image generation unit and may be located in the image generation unit, but may also be located between the image generation unit and the signal unit.

The reception unit 2200 may receive the first signal and the second signal. The reception unit 2200 may include an optical detection element. For example, the reception unit 2200 may include a photo diode, etc., to receive the first signal and the second signal. Moreover, the reception unit 220 may convert the received optical signal into an electrical signal.

The reception unit may also receive a moving distance of the signal unit from the sensor.

The image extraction unit 2300 may calculate an image signal (or an image) by using the first signal and the second signal from the reception unit 2200. Herein, it should be understood that the image signal or the image corresponds to an image provided to the operator and thus will be used interchangeably with an image. Thus, a location of a blood vessel will be described based on an image as shown in the drawings.

In an embodiment, the image extraction unit 2300 may compare a reference signal (or reference light) with a sample signal (or sample light) and generate an image signal through an interference signal resulting from an optical path difference therebetween. A depth location that generates sample light having the same optical path length as an optical path length of the reference light is referred to as a zero delay, and a depth shape at a measurement point of the target (the tissue) appears as a relative location with respect to the zero-delay.

Moreover, the image extraction unit 2300 may include an optical interference optical system to which an OCT technique is applied for an optical signal.

Alternatively, in the image extraction unit 2300, an interference signal may correspond to the above-described scan signal that may be an element (e.g., a slope) of a graph calculated by taking a depth at which the optical signal is reflected from the tissue, as an x axis and a backscattered intensity as a y axis. For example, the operator may perform ablation by easily determining a portion with a rapid change in the slope as an ablation tissue and a portion with a gentle change in the slope as a non-ablation tissue, such that the tissue ablation system according to an embodiment may improve the convenience and accuracy of surgery. In addition, different shades may be expressed according to scattering intensity.

Through various methods described above, the image extraction unit may provide an image representing an inner side of the tissue by using the interference signal.

In particular, the image extraction unit 2300 may compensate for the interference signal by reflecting a moving speed of the signal unit by using the moving distance of the signal unit from the sensor. That is, the moving speed of the signal unit may differ with manipulation of the operator, such that the image extraction unit may extract the image signal or the image by reflecting a different moving speed.

More specifically, the image extraction unit 2300 may calculate the speed of the signal unit by reflecting a time to the moving speed of the signal unit from the sensor, and extract the moving speed of the signal unit per moving distance of the signal unit. The image extraction unit 2300 may apply the extracted moving speed and moving distance of the signal unit to a delay of the interference signal. For example, shifting with respect to time may be performed on the reference signal. By doing so, accurate image extraction may be performed in correspondence to manipulation of the operator.

The image extraction unit 2300 may include a first extraction unit 2310, a second extraction unit 2320, a third extraction unit 2330, and a fourth extraction unit 2340.

The first extraction unit 2310 may calculate a vertical length and a horizontal length of an image in addition to the image by using the first signal, the second signal, and the moving distance of the signal unit sensed by the signal unit.

The first extraction unit 2310 may calculate locations of the first jaw and the second jaw through the first signal and the second signal to calculate the vertical length of the image based on a minimum separation distance, stored in the memory unit 2400, between the first jaw and the second jaw. The first extraction unit 2310 may calculate the vertical length in predetermined units. However, only a unit vertical length or a unit horizontal length are shown in the drawings.

The first extraction unit 2310 may also calculate the horizontal length by using the vertical length. Alternatively, the horizontal length may be calculated from a length of an end of the first jaw or the second jaw (e.g., a length between both ends of the first jaw). Alternatively, the first extraction unit 2310 may calculate the horizontal length in the image by using the moving distance of the signal unit. The first extraction unit 2310 may calculate the horizontal length in predetermined units.

In addition, the second extraction unit 2320 may calculate a location of a blood vessel based on a change of shade in the image representing the inner side of the tissue from the first signal and the second signal. In this case, the change of shade may correspond to a change of backscattered intensity. Thus, the display unit 3000 may display pointing indicating the blood vessel in the periphery of the location of the blood vessel to allow the operator to recognize the blood vessel. Pointing may be performed by display (e.g., a pointer, a circle, etc.), an alarm, etc., in the image. With this configuration, the operator may easily recognize the location of the blood vessel.

The second extraction unit 2320 may detect the speed of blood along with distal or proximal movement of the opening/closing trigger in the manipulation unit. In an embodiment, when the opening/closing trigger moves distally, a blood flow in the blood vessel increases, causing a blur of an image. For example, when the operator moves some opening/closing switch in the locking state, the second extraction unit 2320 may calculate a region where the blur occurs as a location of the blood vessel.

With this structure, the tissue ablation system according to an embodiment may accurately provide the location of the blood vessel to the operator. That is, the first extraction unit may easily calculate a blood vessel of a predetermined size or more, and the second extraction unit may easily calculate a blood vessel of a predetermined size or less.

The second extraction unit 2320 may calculate the speed of blood in the blood vessel based on the blur. The second extraction unit 2320 may calculate the speed of blood from the amount of change in the blur and movement of shade, and provide the speed of the blood to the operator through the display unit. Thus, the operator may more clearly recognize the type of the blood vessel, etc., and prevent an emergency situation occurring during surgery.

Moreover, the second extraction unit 2320 may determine the type of the blood vessel from the speed of the blood. In an embodiment, the second extraction unit 2320 may calculate whether the blood vessel is an artery or a vein (or capillary), based on the speed of the blood. For example, when the speed of the blood in the blood vessel is higher than a reference speed, the second extraction unit 2320 may calculate the blood vessel as an artery.

The display unit 3000 may also display the type of the blood vessel with respect to the location of the blood vessel. Thus, the operator may improve the accuracy and speed of surgery by identifying the type of the blood vessel.

The second extraction unit 2320 may calculate the size of the blood vessel and output ablation function blocking when the size is in a range in which the bleeding may be stopped, that is, the size is greater than or equal to a predetermined size. That is, irradiation of a laser may be blocked.

Moreover, the second extraction unit 2320 may output an alarm for warning that the blood vessels in the tissue are not accurately held (captured) by the ablation unit, when the blood vessels do not overlap between the first jaw and the second jaw in the longitudinal direction. Thus, the operator may control the ablation unit to change a location where the tissue is captured, thereby improving the accuracy of surgery.

The third extraction unit 2330 may calculate locations of lymphatic vessels and nerves in the blood vessel as well as the location of the blood vessel. The third extraction unit 2330 may calculate the location of the blood vessel as described above. In an embodiment, the third extraction unit 2330 may calculate, as the location of the lymphatic vessel, a region where a change in shade occurs in a region other than the blood vessel, or a region where a blur occurs, but a fluid moving speed that is different from the blood vessel is calculated. Since lymph fluid moves at a lower speed than blood, the amount of change in the blur may also be small. Thus, the third extraction unit 2330 may extract the location of the blood vessel as the location of the lymphatic vessel based on the amount of change in the blur in the location of the blood vessel. In addition, the location of the nerve may be calculated as a shade difference.

The fourth extraction unit 2340 may calculate energy, such as a laser, etc., irradiated to ablate the tissue according to the size of the blood vessel. That is, the tissue ablation system according to an embodiment may accurately and quickly ablate an ablation area by adjusting energy irradiated to the tissue in correspondence to the size of the blood vessel.

The display unit 3000 may be connected to the image generation unit 2000 to image a signal (e.g., the optically interfered signal) output from the image generation unit 2000. In this case, the display unit 3000 may image the signal into an ablation area and a non-ablation area of the tissue and provide them to the operator.

The display unit 3000 may be implemented in various display manners such as liquid crystals, plasma, a light-emitting diode, an organic light-emitting diode, a surface-conduction electron-emitter, a carbon nano-tube, nano-crystal, etc.

At this time, as described above, since the signal unit is disposed on a side surface of the first jaw, the operator may check a location of an ablation tissue on a side surface with the naked eye, and at the same time, check existence/absence of a blood vessel, etc., inside the tissue, thus being able to make a right decision on ablation. Consequently, an accident such as unintentional vascular resection, etc., may be prevented. Moreover, the tissue ablation system according to an embodiment may provide an image enabling the ablation area/the non-ablation area to be easily distinguished without a photographing device such as a camera, etc.

The tissue ablation device or the tissue ablation system including the same according to the present disclosure may have a structure removably connected to an external device that images a tissue, such that when the tissue ablation device is damaged, it may be easily replaced and rephotographing may be immediately performed, thereby increasing the efficiency of laparoscopic surgery.

Moreover, the tissue ablation device or the tissue ablation system including the same as described above may easily observe the existence/absence of a blood vessel and a size of the blood vessel with the naked eye through an image of an internal structure of a tissue to be ablated, thereby minimizing a damage caused by unintentional vascular resection in a surgical operation.

That is, by using the tissue ablation device to which a module for imaging an inner side of a tissue to determine the existence/absence of a blood vessel inside an ablation tissue in laparoscopic surgery, a clinician may prevent unintentional vascular resection and perform safe tissue ablation through an image of an internal structure of the tissue to be ablated on a monitor.

In exemplary embodiments of the present invention, the term ' . . . unit', as used herein, denotes a software or hardware component, such as a Field Programmable Gate Array (FPGA) or Application Specific Integrated Circuit (ASIC), which performs certain tasks. However, the meaning of ' . . . unit' is not limited to software or hardware. ' . . . unit' may advantageously be configured to reside on the addressable storage medium and configured to reproduce one or more processors. Thus, a unit may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and ' . . . unit(s)' may be combined into fewer components and ' . . . unit(s)' or further separated into additional components and ' . . . unit(s)'. In addition, components and ' . . . unit(s)' may be implemented to execute one or more CPUs in a device or a secure multi-media card.

While the embodiments have been described, they are merely examples and do not limit the present invention, and it would be understood by those of ordinary skill in the art that several modifications and applications not described above are possible without departing the essential characteristics of the current embodiment. For example, each component described in detail in the embodiment may be carried out by being modified. Differences related to such modifications and applications should be interpreted as falling within the scope of the present invention defined in the appended claims.

The invention claimed is:

1. An ablation device comprising:
a first jaw;
a second jaw comprising an ablation unit comprising a protrusion for ablating a tissue and being rotatable with respect to the first jaw under the first jaw; and
a signal unit configured to provide a signal to the tissue and receive a reflected signal and disposed on the second jaw,
wherein the signal unit moves in a longitudinal direction of the ablation unit,
wherein the first jaw does not overlap the signal unit in a vertical direction,
wherein the second jaw overlaps the signal unit in the vertical direction,
wherein the second jaw comprises a recess in which the ablation unit is nested and a protrusion unit located on a side thereof,
wherein the signal unit is disposed on the protrusion unit,
wherein an upper surface of the ablation unit is disposed above the protrusion, and
wherein the signal unit overlaps the ablation unit in a direction perpendicular to both the vertical direction and the horizontal direction.

2. The ablation device of claim 1, wherein the signal unit comprises:
a first signal region overlapping the protrusion unit in the vertical direction; and
a second signal region overlapping the ablation unit in the vertical direction.

3. The ablation device of claim 1, wherein the first jaw comprises a first region overlapping the ablation unit in the vertical direction, and
an outer surface of the first jaw has a first curvature in the first region.

4. The ablation device of claim 3, wherein an outer surface of the second jaw has a second curvature in a lower portion of the first region, and
an outer surface of the signal unit has a third curvature in a lower portion of the first region.

5. The ablation device of claim 4, wherein the first curvature, the second curvature, and the third curvature are equal to one another.

6. The ablation device of claim 1, wherein the first jaw comprises a first outer surface and a second outer surface which extend in the longitudinal direction and face each other,
the second jaw comprises a first edge surface and a second edge surface which extend in the longitudinal direction and face each other,
a first separation distance between the first outer surface and the first edge surface is less than a second separation distance between the second outer surface and the second edge surface, and
the signal unit is disposed between the second outer surface and the second edge surface.

7. The ablation device of claim 1, wherein the signal unit moves in the longitudinal direction between both end portions of the ablation unit.

8. The ablation device of claim 1, wherein the signal unit comprises a transfer unit through which the signal moves and a transceiving unit configured to emit the signal moving from the transfer unit to the tissue and receive the reflected signal.

9. The ablation device of claim 8, wherein the transceiving unit comprises:
a mirror reflecting the signal toward the tissue; and
a lens unit emitting the tissue reflected from the mirror toward the tissue.

10. The ablation device of claim 8, wherein the signal unit further comprises
a reflection member located in an end portion thereof apart from the transfer unit and the transceiving unit, and
the reflection member reflects the signal emitted from the transceiving unit to the tissue.

11. The ablation device of claim 10, wherein the signal unit comprises a first signal unit and a second signal unit that are provided in plural, and
the first signal unit and the second signal unit move in the longitudinal direction in different ranges with respect to the tissue.

12. The ablation device of claim 11, wherein the first signal unit is disposed between the second signal unit and the first jaw, and
a length of the first signal unit in the longitudinal direction is less than a length of the second signal unit in the longitudinal direction.

13. A tissue ablation device comprising:
an ablation device configured to ablate a tissue;
an extension unit connected to the ablation device; and a manipulation member configured to manipulate an operation of the ablation device;

a first jaw;

a second jaw comprising an ablation unit comprising a protrusion for ablating a tissue and being rotatable with respect to the first jaw under the first jaw; and a signal unit configured to provide a signal to the tissue and receive a reflected signal and disposed on the second jaw, wherein the signal unit moves in a longitudinal direction of the ablation unit, the first jaw does not overlap the signal unit in a vertical direction, and the second jaw overlaps the signal unit in the vertical direction, wherein the second jaw comprises a recess in which the ablation unit is nested and a protrusion unit located on a side thereof, wherein the signal unit is disposed on the protrusion unit, wherein an upper surface of the ablation unit is disposed above the protrusion, and wherein the signal unit overlaps the ablation unit in a direction perpendicular to both the vertical direction and the horizontal direction.

14. A tissue ablation system comprising:

a tissue ablation device comprising an ablation device configured to ablate a tissue;

an image generation unit configured to provide a signal to the tissue ablation device, receive a signal reflected from the tissue, and output an image signal; and a display unit configured to receive and display the image signal, wherein the ablation device comprises:

a first jaw;

a second jaw comprising an ablation unit comprising a protrusion for ablating a tissue and being rotatable with respect to the first jaw under the first jaw; and a signal unit configured to provide a signal to the tissue and receive a reflected signal and disposed on the second jaw, wherein the signal unit moves in a longitudinal direction of the ablation unit, the first jaw does not overlap the signal unit in a vertical direction, and the second jaw overlaps the signal unit in the vertical direction, wherein the second jaw comprises a recess in which the ablation unit is nested and a protrusion unit located on a side thereof, wherein the signal unit is disposed on the protrusion unit, wherein an upper surface of the ablation unit is disposed above the protrusion, and wherein the signal unit overlaps the ablation unit in a direction perpendicular to both the vertical direction and the horizontal direction.

* * * * *